(12) United States Patent
Brahmasandra et al.

(10) Patent No.: US 9,382,532 B2
(45) Date of Patent: Jul. 5, 2016

(54) METHOD AND MATERIALS FOR ISOLATION OF NUCLEIC ACID MATERIALS

(71) Applicant: NeuMoDx Molecular, Inc., Ann Arbor, MI (US)

(72) Inventors: Sundaresh Brahmasandra, Ann Arbor, MI (US); Michelle Mastronardi, Ann Arbor, MI (US); Elizabeth Craig, Ann Arbor, MI (US); Maureen Carey, Ann Arbor, MI (US)

(73) Assignee: NeuMoDx Molecular, Inc., Ann Arbor, MI (US)

( * ) Notice: Subject to any disclaimer, the term of this patent is extended or adjusted under 35 U.S.C. 154(b) by 0 days.

(21) Appl. No.: 14/168,760

(22) Filed: Jan. 30, 2014

(65) Prior Publication Data
US 2014/0147892 A1    May 29, 2014

Related U.S. Application Data

(63) Continuation of application No. 14/060,214, filed on Oct. 22, 2013, now abandoned.

(60) Provisional application No. 61/718,634, filed on Oct. 25, 2012.

(51) Int. Cl.
C12Q 1/68       (2006.01)
C12N 15/10      (2006.01)

(52) U.S. Cl.
CPC ........ *C12N 15/1013* (2013.01); *C12N 15/1006* (2013.01)

(58) Field of Classification Search
CPC ...... B82Y 15/00; B82Y 30/00; C12N 15/101; C12Q 1/6813
See application file for complete search history.

(56) References Cited

U.S. PATENT DOCUMENTS

| 776,747 A | 12/1904 | Kling |
|---|---|---|
| 778,036 A | 12/1904 | Hepp et al. |
| 3,963,151 A | 6/1976 | North |

(Continued)

FOREIGN PATENT DOCUMENTS

| CN | 101432698 A | 5/2009 |
|---|---|---|
| CN | 1773190 B | 5/2010 |

(Continued)

OTHER PUBLICATIONS

Compton, Cancer and Metastasis Rev., vol. 11, pp. 105-119 (1992).*

*Primary Examiner* — Robert T Crow
(74) *Attorney, Agent, or Firm* — Jeffrey Schox; Ivan Wong

(57) ABSTRACT

A method for nucleic acid isolation comprising: receiving a binding moiety solution within a process chamber; mixing the binding moiety solution with a biological sample, within the process chamber, in order to produce a moiety-sample mixture; incubating the moiety-sample mixture during a time window, thereby producing a solution comprising a set of moiety-bound nucleic acid particles and a waste volume; separating the set of moiety-bound nucleic acid particles from the waste volume; washing the set of moiety-bound nucleic acid particles; and releasing a nucleic acid sample from the set of moiety-bound nucleic acid particles. The method preferably utilizes a binding moiety comprising at least one of poly(allylamine) and polypropylenimine tetramine dendrimer, both of which reversibly bind and unbind to nucleic acids based upon environmental pH.

20 Claims, 14 Drawing Sheets

(56) References Cited

U.S. PATENT DOCUMENTS

| | | | |
|---|---|---|---|
| 5,681,529 A | 10/1997 | Taguchi et al. | |
| 5,725,831 A | 3/1998 | Reichler et al. | |
| 5,750,338 A | 5/1998 | Collins et al. | |
| 5,783,148 A | 7/1998 | Cottingham et al. | |
| 5,824,478 A * | 10/1998 | Muller | 435/6.12 |
| 5,853,667 A | 12/1998 | Seaton et al. | |
| 6,168,948 B1 | 1/2001 | Anderson et al. | |
| 6,331,266 B1 | 12/2001 | Powell et al. | |
| 6,368,871 B1 | 4/2002 | Christel et al. | |
| 6,374,684 B1 | 4/2002 | Dority | |
| 6,374,685 B1 | 4/2002 | Daly | |
| 6,431,476 B1 | 8/2002 | Taylor et al. | |
| 6,440,725 B1 | 8/2002 | Pourahmadi et al. | |
| 6,664,104 B2 | 12/2003 | Pourahmadi et al. | |
| 6,692,700 B2 | 2/2004 | Handique | |
| 6,852,287 B2 | 2/2005 | Ganesan | |
| 6,860,993 B2 | 3/2005 | Effenhauser et al. | |
| 6,872,315 B2 | 3/2005 | Effenhauser et al. | |
| 6,878,540 B2 | 4/2005 | Pourahmadi et al. | |
| 6,893,879 B2 | 5/2005 | Petersen et al. | |
| 6,899,838 B2 | 5/2005 | Lastovich | |
| 6,987,018 B2 | 1/2006 | Taylor et al. | |
| 7,052,268 B2 | 5/2006 | Powell et al. | |
| 7,135,144 B2 | 11/2006 | Christel et al. | |
| 7,192,557 B2 | 3/2007 | Wu et al. | |
| 7,270,786 B2 | 9/2007 | Parunak et al. | |
| 7,323,140 B2 | 1/2008 | Handique et al. | |
| 7,332,130 B2 | 2/2008 | Handique | |
| 7,569,346 B2 | 8/2009 | Petersen et al. | |
| 7,674,431 B2 | 3/2010 | Ganesan | |
| 7,682,820 B2 | 3/2010 | Bader | |
| 7,731,906 B2 | 6/2010 | Handique et al. | |
| 7,738,094 B2 | 6/2010 | Goldberg | |
| 7,763,209 B2 | 7/2010 | Haley | |
| 7,767,447 B2 | 8/2010 | Breidenthal et al. | |
| 7,820,030 B2 | 10/2010 | Althaus et al. | |
| 7,906,758 B2 * | 3/2011 | Stults et al. | 250/282 |
| 7,914,994 B2 | 3/2011 | Petersen et al. | |
| 7,935,537 B2 | 5/2011 | Haley | |
| 7,955,798 B2 | 6/2011 | Mauritz | |
| 7,955,864 B2 | 6/2011 | Cox et al. | |
| 7,964,413 B2 | 6/2011 | Macioszek et al. | |
| 7,987,022 B2 | 7/2011 | Handique et al. | |
| 7,995,798 B2 | 8/2011 | Krupnik et al. | |
| 7,998,708 B2 | 8/2011 | Handique et al. | |
| 8,003,329 B2 | 8/2011 | Macevicz | |
| 8,008,066 B2 | 8/2011 | Lair et al. | |
| 8,043,581 B2 | 10/2011 | Ganesan | |
| 8,048,375 B2 | 11/2011 | Breidenthal et al. | |
| 8,048,386 B2 | 11/2011 | Dority et al. | |
| 8,052,929 B2 | 11/2011 | Breidenthal et al. | |
| 8,088,616 B2 | 1/2012 | Handique | |
| 8,105,477 B2 | 1/2012 | Althaus et al. | |
| 8,105,783 B2 | 1/2012 | Handique | |
| 8,110,158 B2 | 2/2012 | Handique | |
| 8,133,671 B2 | 3/2012 | Williams et al. | |
| 8,168,134 B2 | 5/2012 | Lehto | |
| 8,182,763 B2 | 5/2012 | Duffy et al. | |
| 8,183,359 B2 | 5/2012 | Becker et al. | |
| 8,187,557 B2 | 5/2012 | Van et al. | |
| 8,247,176 B2 | 8/2012 | Petersen et al. | |
| 8,248,597 B2 | 8/2012 | Goldberg | |
| 8,268,245 B2 | 9/2012 | Wahl | |
| 8,268,603 B2 | 9/2012 | Taylor et al. | |
| 8,273,308 B2 | 9/2012 | Handique et al. | |
| 8,287,820 B2 | 10/2012 | Williams et al. | |
| 8,288,520 B2 | 10/2012 | Eder et al. | |
| 8,323,584 B2 | 12/2012 | Ganesan | |
| 8,323,900 B2 | 12/2012 | Handique et al. | |
| 8,324,372 B2 | 12/2012 | Brahmasandra et al. | |
| 8,349,564 B2 | 1/2013 | Macioszek et al. | |
| 8,394,336 B2 | 3/2013 | Curcio | |
| 8,404,198 B2 | 3/2013 | Amshey et al. | |
| 8,415,103 B2 | 4/2013 | Handique | |
| 8,420,015 B2 | 4/2013 | Ganesan et al. | |
| 8,431,413 B2 | 4/2013 | Dority et al. | |
| 8,440,149 B2 | 5/2013 | Handique | |
| 8,470,586 B2 | 6/2013 | Wu et al. | |
| 8,470,588 B2 | 6/2013 | Boehm et al. | |
| 8,473,104 B2 | 6/2013 | Handique et al. | |
| 8,480,976 B2 | 7/2013 | Breidenthal et al. | |
| 8,491,178 B2 | 7/2013 | Breidenthal et al. | |
| 8,501,461 B2 | 8/2013 | Knight et al. | |
| 8,640,555 B2 | 2/2014 | Zenhausern et al. | |
| 8,709,787 B2 | 4/2014 | Handique | |
| 9,101,930 B2 | 8/2015 | Williams et al. | |
| 2002/0039783 A1 | 4/2002 | McMillan et al. | |
| 2002/0160518 A1 | 10/2002 | Hayenga et al. | |
| 2003/0170686 A1 * | 9/2003 | Hoet et al. | 435/6 |
| 2004/0018611 A1 | 1/2004 | Ward et al. | |
| 2004/0138154 A1 | 7/2004 | Yu et al. | |
| 2005/0180891 A1 | 8/2005 | Webster et al. | |
| 2005/0205199 A1 | 9/2005 | Green | |
| 2005/0221529 A1 | 10/2005 | Bang et al. | |
| 2005/0233370 A1 | 10/2005 | Ammann et al. | |
| 2005/0250199 A1 | 11/2005 | Anderson et al. | |
| 2005/0272169 A1 | 12/2005 | Griffin et al. | |
| 2006/0068204 A1 * | 3/2006 | Rasmussen et al. | 428/407 |
| 2006/0166233 A1 * | 7/2006 | Wu et al. | 435/6 |
| 2006/0182300 A1 | 8/2006 | Schwartz | |
| 2006/0182842 A1 | 8/2006 | Pruden et al. | |
| 2007/0148174 A1 | 6/2007 | Kudlicki et al. | |
| 2007/0184463 A1 | 8/2007 | Molho et al. | |
| 2007/0190662 A1 | 8/2007 | Baetzold et al. | |
| 2007/0196912 A1 | 8/2007 | Facer et al. | |
| 2007/0292941 A1 | 12/2007 | Handique et al. | |
| 2008/0057572 A1 | 3/2008 | Petersen et al. | |
| 2008/0146896 A1 | 6/2008 | Rabinowitz et al. | |
| 2008/0193384 A1 * | 8/2008 | Willard et al. | 424/9.363 |
| 2008/0200343 A1 | 8/2008 | Clemens et al. | |
| 2008/0241569 A1 * | 10/2008 | Qin et al. | 428/548 |
| 2008/0275409 A1 | 11/2008 | Kane et al. | |
| 2008/0280285 A1 | 11/2008 | Chen et al. | |
| 2009/0130719 A1 | 5/2009 | Handique | |
| 2009/0131650 A1 * | 5/2009 | Brahmasandra et al. | 536/25.4 |
| 2009/0215125 A1 | 8/2009 | Reed et al. | |
| 2009/0275014 A1 | 11/2009 | Maltezos et al. | |
| 2010/0009351 A1 | 1/2010 | Brahmasandra et al. | |
| 2010/0009375 A1 | 1/2010 | Sherman et al. | |
| 2010/0029544 A1 * | 2/2010 | Cheng et al. | 514/3 |
| 2010/0075311 A1 | 3/2010 | Barrault et al. | |
| 2010/0165784 A1 | 7/2010 | Jovanovich et al. | |
| 2010/0300563 A1 | 12/2010 | Ramunas et al. | |
| 2010/0303687 A1 | 12/2010 | Blaga et al. | |
| 2010/0310423 A1 | 12/2010 | Nieuwenhuis | |
| 2010/0323919 A1 | 12/2010 | Chen et al. | |
| 2011/0003281 A1 | 1/2011 | Woudenberg et al. | |
| 2011/0053289 A1 | 3/2011 | Lowe et al. | |
| 2011/0071031 A1 * | 3/2011 | Khripin et al. | 506/7 |
| 2011/0201099 A1 | 8/2011 | Anderson et al. | |
| 2011/0318840 A1 | 12/2011 | Ziglioli et al. | |
| 2012/0046203 A1 | 2/2012 | Walsh et al. | |
| 2012/0245218 A1 | 9/2012 | Fukushima et al. | |
| 2012/0245337 A1 | 9/2012 | Fabis et al. | |
| 2013/0210015 A1 | 8/2013 | Williams et al. | |
| 2013/0210127 A1 | 8/2013 | Williams et al. | |

FOREIGN PATENT DOCUMENTS

| | | |
|---|---|---|
| WO | 2007064635 A1 | 6/2007 |
| WO | 2009022994 | 4/2009 |

* cited by examiner

METHOD AND MATERIALS FOR ISOLATION OF NUCLEIC ACID MATERIALS

CROSS-REFERENCE TO RELATED APPLICATIONS

This application claims the benefit of U.S. Provisional Application Ser. No. 61/718,634 filed 25 Oct. 2012, which is incorporated in its entirety herein by this reference.

TECHNICAL FIELD

This invention relates generally to the biotechnology field, and more specifically to an improved method and materials for isolation of nucleic acid materials.

BACKGROUND

Molecular diagnostics is a clinical laboratory discipline that has developed rapidly during the last 25 years. It originated from basic biochemistry and molecular biology research procedures, but now has become an independent discipline focused on routine analysis of nucleic acids (NA), including deoxyribonucleic acid (DNA) and ribonucleic acid (RNA) for diagnostic use in healthcare. Molecular diagnostic analysis of biological samples can include the detection of one or more nucleic acid materials present in the specimen. The particular analysis performed may be either qualitative and/or quantitative. Methods of analysis involve isolation and purification of nucleic acid material, and an important step in the sensitive and rapid detection of a nucleic acid is the isolation and purification of said nucleic acid material from the crude biological sample. Often, a nucleic acid material sample is obtained in insufficient quantity, quality, and/or purity, hindering a robust implementation of an analytical technique. Furthermore, methods of isolation are specific to certain clinical matrices containing the nucleic acid and not applicable across multiple matrices. Due to these and other deficiencies of current methods and materials used in isolation of nucleic acid materials, there is thus a need for an improved method and materials for isolation of nucleic acid materials.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method for Nucleic Acid Isolation

Figure 1A:
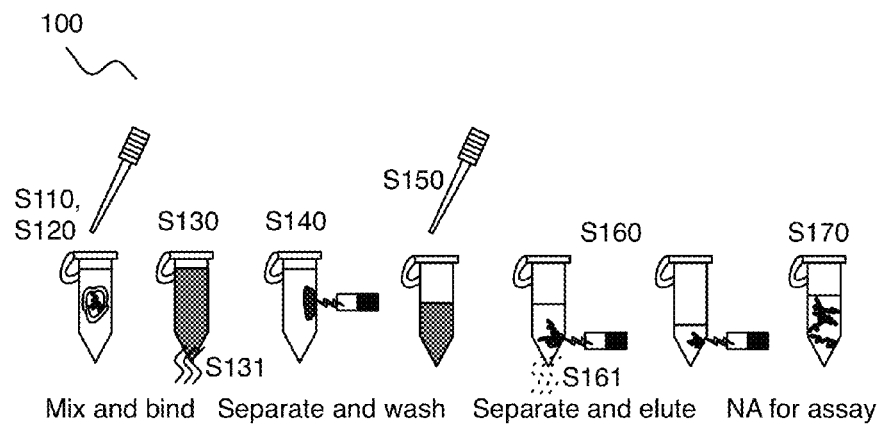
FIGS. 1A-1C depict embodiments of process flow of a method for isolation of nucleic acid materials.
Figure 2:
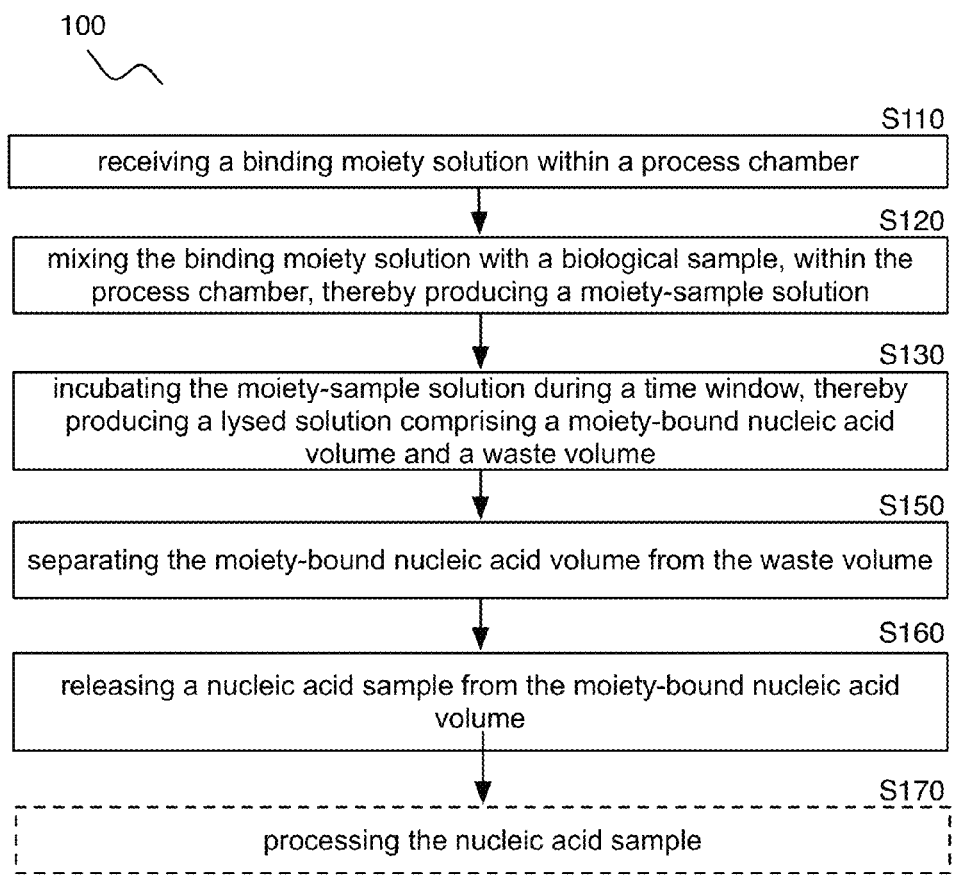
FIG. 2 depicts a flow chart of a method for isolation of nucleic acid materials.

As shown in FIGS. 1A and 2, a method 100 for nucleic acid isolation comprises receiving a binding moiety solution within a process chamber S110; mixing the binding moiety solution with a biological sample, within the process chamber, in order to produce a moiety-sample solution S120; incubating the moiety-sample solution during a time window S130, thereby producing a lysed solution comprising a moiety-bound nucleic acid volume and a waste volume; separating the moiety-bound nucleic acid volume from the waste volume S140; washing the moiety-bound nucleic acid volume S150; and releasing a nucleic acid sample from the moiety-bound nucleic acid volume S160. The method functions to liberate, extract, aggregate, and/or isolate nucleic acids (e.g., deoxyribonucleic acids, ribonucleic acids) from a raw biological sample (e.g., directly from a subject or agricultural product), wherein the raw biological sample contains the nucleic acids in bound-form (e.g., bound in cellular form). The method 100 can also serve as a precursor to other processing methods for nucleic acids, including amplification (e.g., by polymerase chain reaction) and/or characterization (e.g., by fluorescence detection) of nucleic acids from a biological sample. The method 100 preferably enables the preferential binding of a desired nucleic acid sample, as compared to binding of inhibitors (e.g., membrane fragments, humic acids, mucousal compounds, hemoglobin, proteins) or non-preferred substances, or the preferential washing away of inhibitors/non-preferred substances as compared to the desired nucleic acid sample. The method 100 also preferably enables the release or elution of the desired nucleic acid sample from the microparticle or other surface for further processing and/or characterization.

The method 100 can be performed in any container or process chamber that is configured to contain a suitable concentration of affinity moiety-coated microparticles, facilitate suitable buffer conditions to allow for binding (e.g., buffer conditions providing a suitably low pH), contain suitable amounts of proteolytic or other enzymes for effective lysis or removal of inhibitory substances, and provide suitable thermal conditions that collectively enable binding of nucleic acids to the affinity moiety-coated microparticles. The process chamber or any other device can also be configured to enable another set of conditions (e.g., suitably high pH, suitably low salt concentration, and/or suitably high temperature) that facilitate release of bound nucleic acids. Suitable conditions for binding and release can vary between different biological sample types, and example suitable conditions for exemplary biological sample types are described in further detail in Section 3 below.

In a specific example, as shown in FIG. 1A, the method 100 can be implemented using a 1.7 mL microcentrifuge tube; however, the method 100 can alternatively be implemented using any suitable tube, vessel, container, chamber, or device. In other examples, the method 100 can be implemented using the system described in U.S. patent application Ser. No. 13/766,359 (U.S. Pat. App. Pub. No. 2013/0210127 A1), entitled "System and Method for Processing and Detecting Nucleic Acids", and/or the cartridge described in U.S. patent application Ser. No. 13/765,996 (U.S. Pat. App. Pub. No. 2013/0210125 A1), entitled "Microfluidic Cartridge for Processing and Detecting Nucleic Acids", which are both incorporated herein in their entirety by this reference.

Step S110 recites receiving a binding moiety solution within a process chamber, and functions to provide an environment that facilitates binding of nucleic acids to a binding moiety. Preferably, the binding moiety solution comprises a suitable concentration of an affinity moiety configured to selectively bind to target nucleic acids, such as an affinity moiety described in Section 2 below; however, the binding moiety solution can additionally or alternatively comprise additional components, such as a collection buffer (e.g., low pH buffer, high salt content buffer), proteolytic enzymes (e.g., Proteinase K, other proteases), additional lysis reagents, and/or any other suitable process reagents that facilitate binding of nucleic acids to the affinity moieties. Furthermore, amounts/concentrations of proteolytic enzymes (e.g., Proteinase K, other proteases) within the binding moiety solution can be optimized to provide a suitable level of proteolytic action while reducing carry-over of the proteolytic enzymes into further process steps (e.g., when using elution solutions with lower salt concentrations). Reducing carry-over of proteolytic enzymes provides significantly better amplification and subsequent fluorescence signal (e.g., nucleic acid detection) in variations of Step S170. In specific examples, the amount of Proteinase K in a binding moiety solution can range from 20-40 microliters of 20 mg/mL Proteinase K. In one variation, the affinity moieties are coated onto the surfaces of microparticles by covalent bonding, and are configured to facilitate further processing and isolation of nucleic acids bound to the affinity moieties. Furthermore, in this variation, the amount of affinity moiety coated onto the microparticles is preferably configured to provide a high binding capacity with a reduced amount of microparticles (e.g., configured to provide a binding capacity of 25-100 micrograms of nucleic acids per 1 mg of microparticles). Such a configuration allows release of nucleic acids into a small volume, in order to efficiently concentrate a target nucleic acid from a biological sample.

In a specific example of this variation of Step S110, the microparticles are magnetic beads (e.g., magnetic, parmagnetic, superparamagnetic) with any suitable hydrophilicity (e.g., hydrophobic, hydrophilic), wherein the magnetic beads are coated with the affinity moiety and simultaneously received within the process chamber along with a low-pH buffer solution, proteolytic enzymes, and lytic reagents. In this specific example, magnetic separation can be used to facilitate further processing and isolation of nucleic acids bound to the affinity moieties coupled to magnetic beads. In another specific example of this variation, the microparticles are beads of a suitable size coated with the affinity moiety, and are simultaneously received within the process chamber along with a suitable buffer solution, proteolytic enzymes, and lytic reagents. In this specific example, sized-based separation can be used to facilitate further processing and isolation of nucleic acids bound to the affinity moieties coupled to the suitably-sized beads. The binding moiety solution of Step S110 can additionally or alternatively comprise any suitable affinity moiety or combination of affinity moiety delivered by any suitable mechanism or substrate.

Figure 1B:
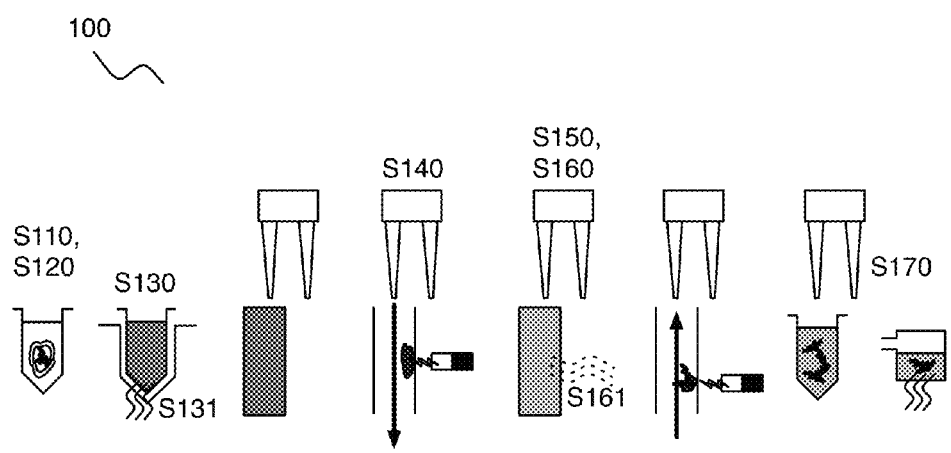
Figure 1C:
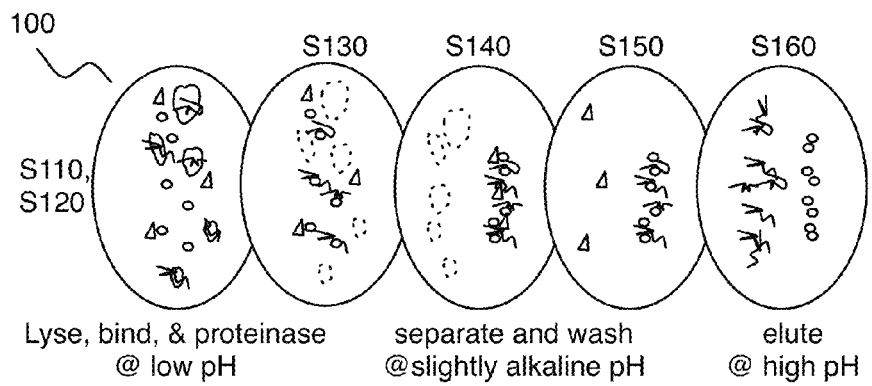

Step S120 recites mixing the binding moiety solution with a biological sample, within the process chamber, in order to produce a moiety-sample solution, which functions to initiate lysis of the biological sample and enable target nucleic acids to bind to affinity moieties of the binding moiety solution. Preferably, binding of target nucleic acids to affinity moieties is facilitated by the appropriate pH of the binding solution, as shown in FIG. 1C; however, binding can be facilitated by any other suitable mechanism. In a variation involving an appropriate pH in the binding solution, mixing and binding can occur at a low pH, which produces a positively charged affinity moiety that is attracted to negatively charged nucleic acid molecules. Specific examples of affinity moieties that function via a pH shift are described in Section 2 below.

In Step S120, the process chamber can be any suitable vessel, as shown in FIG. 1A, or a suitable capture plate, such as that described in U.S. patent application Ser. No. 13/766,359, entitled "System and Method for Processing and Detecting Nucleic Acids", as shown in FIG. 1B. Preferably, the biological sample is delivered into the process chamber containing the binding moiety solution, and the resulting moiety-sample solution is aspirated and dispensed repeatedly to thoroughly mix the moiety-sample solution. Alternatively, the biological sample and the binding moiety solution can be mixed in any suitable order, and can be aspirated and dispensed any suitable number of times to mix the moiety-sample solution. Furthermore, in other variations, the moiety-sample solution can be transferred to any other suitable fluid vessel for mixing. In a specific example, between 5 uL-2 mL of biological sample is delivered to the process chamber containing the binding moiety solution and the resulting moiety-sample solution is then mixed thoroughly by aspirating and dispensing the moiety-sample solution ten times to ensure uniform distribution within the moiety-sample solution.

In Step S120, the biological sample can comprise any suitable sample containing polynucleotides, including deoxyribonucleic acids (DNA) and/or ribonucleic acids (RNA), and can be co-delivered in any suitable matrix or medium. In variations of Step S120, the biological sample can comprise biological specimens from any species, and in specific examples wherein the biological specimen is from an animal species, the biological sample can comprise any of cerebrospinal fluid (CSF), a mucous membrane sample (e.g., nasal swab, buccal swab, vaginal tissue swab), blood (e.g., whole blood, dried blood), organ tissue (e.g., biopsy aspirate), plasma, urine, feces, skin, hair, or any other biological sample carried in matrix or media (e.g., universal transport media). In these variations and examples, the target nucleic acid(s) of interest can be contained within particles (e.g., cells), tissue fragments, bacteria, fungi, or spores of the biological sample.

Step S130 recites incubating the moiety-sample solution during a time window, and functions to produce a lysed moiety-sample solution comprising a moiety-bound nucleic acid volume (e.g., a volume of nucleic acids reversibly bonded to the set of affinity moiety-coated microparticles) and a waste volume. In Step S130, the moiety-sample solution can be incubated using any suitable heating apparatus, as shown in FIG. 1A, or a suitable capture plate heater, such as that described in U.S. patent application Ser. No. 13/766,359, entitled "System and Method for Processing and Detecting Nucleic Acids", as shown in FIG. 1B. In Step S130, the nucleic acid is released from within the cell or other structure that it is contained within, and binds to the microparticles coupled with the affinity moiety, while other unbound components form a waste volume for later removal, as shown in FIG. 1C. Preferably, the process chamber containing the moiety-sample solution (e.g., lysis, clean-up, binding reagents and the biological sample) is incubated for a defined period of time at a temperature preferably in the range of 25-95 C, wherein time and temperature parameters are biological sample-dependent. Example parameters for different biological samples are described briefly below, and further in Section 3 below. Alternatively, the moiety-sample solution can be transferred to another vessel for incubation in variations of Step S130. Furthermore, in variations of Steps S110, S120, and S130, any or all of the lysis, proteolytic and binding steps can occur simultaneously in the process chamber or any other suitable vessel, and are not required to be discrete steps.

In examples of Step S130, incubation of the moiety-sample solution can be performed for a period of 2-20 minutes depending on the biological specimen and the source(s) of the target nucleic acid(s). Additionally, in the examples, the incubation temperature is based upon the specimen being processed and the source(s) of the target nucleic acid(s). In a first example of Step S130, enteroviral particles are incubated and lysed at room temperature in the presence of detergent. In a variation of the first example, enteroviral particles treated with Proteinase K can be incubated and lysed within a modified temperature range of 37-60 C for optimal activity of the proteinase enzyme. In a second example of Step S130, a nasal swab containing Staphylococcus aureus bacteria is incubated at approximately 95 C to ensure thorough lysis of the gram-positive bacteria. In variations of the second example, treatment of the bacterial sample with specific lytic enzymes (e.g., achromopeptidase or lysostaphin) can result in modified lysis temperature. In all of the specific examples and variations, the incubation produces a lysed moiety-sample solution comprising a volume of affinity moiety-bound nucleic acids and a waste volume for removal.

Step S130 can further comprise Step S131, which recites pre-treating and/or performing additional heating of the moiety-sample solution. Step S131 functions to further facilitate or enhance lysis of the moiety-sample solution. In one application, certain tough-to-lyse organisms (e.g., mycobacteria) can require additional pre-treatment or heating steps, as provided by Step S131, to ensure thorough lysis and subsequent release of the nucleic acid from the organism/biological sample. Preferably, the binding of the target nucleic acid is neither adversely nor positively impacted by the presence of the additional lysis and proteolytic reagents provided in Step S131; however, in alternative variations, binding can be influenced by the additional reagents provided in Step S131, and effects of the reagents can be mitigated or unmitigated depending upon the application and/or desired usage of the target nucleic acid(s).

Step S140 recites separating the moiety-bound nucleic acid volume from the waste volume, and functions to compact or concentrate microparticles coupled to the target nucleic acid(s), by way of the affinity moieties, in order to facilitate removal of the waste volume from the moiety-bound nucleic acid volume. Preferably, the moiety-bound nucleic acid volume is separated using a magnetic-separation method; however the moiety-bound nucleic acid volume can alternatively be separated using methods based upon microparticle size, mass, and/or density (e.g., centrifugation, sedimenting, filtering), and/or focusing methods (e.g., electric field focusing, laser based focusing). Separation in Step S140 can, however, be performed using any other suitable method. In a first variation, wherein the microparticles coupled with affinity moieties have magnetic properties, a magnetic field can be applied to retain the nucleic acid-bound microparticles of the moiety-bound nucleic acid volume, while the waste volume (e.g., cellular debris and other unbound material) is substantially removed by aspiration. In a second variation, wherein the microparticles coupled with affinity moieties have a characteristic dimension for size-based separation, the lysed moiety-sample solution can be filtered to substantially remove the waste volume. In the second variation, the filter is preferably configured to pass the microparticles bound to the target nucleic acids while retaining the waste; however, the filter can alternatively be configured to retain the microparticles while passing the waste.

Preferably, in Step S140, appropriate care is taken to ensure that the compacted microparticles of the moiety-bound nucleic acid volume are not disturbed and no significant loss of the microparticles with bound nucleic acids occurs during removal of the waste volume. Furthermore, in some variations, some liquid can still be retained by the compacted microparticles of the moiety-bound nucleic acid volume in order to minimize microparticle loss. However, some applications of Step S140 can alternatively involve a reduction in retained liquid at the expense of some amount of microparticle loss. In a specific example, the liquid retained can bring the moiety-bound nucleic acid volume to approximately 5-10 microliters.

In Step S140, the lysed moiety-sample solution can be processed within the process chamber to separate the moiety-bound nucleic acid volume from the waste volume; however, the lysed moiety-sample solution can alternatively be transferred to another suitable vessel for separation of the moiety-bound nucleic acid volume from the waste volume. In a first variation, a pipetting system (automatic or manual) can be used to remove the waste volume (e.g., supernatant liquid), and multiple aspirations by the pipetting system may be necessary to ensure as complete a removal of the supernatant as possible. In an example of the first variation, a 1000 microliter pipette tip can be used to perform gross removal of the waste volume in a first aspiration followed by the use of a finer pipette tip (e.g., 100-200 microliter tip) in additional aspirations, to remove the remainder of the waste volume. In the example, the removal of the waste volume occurs close to the bottom of the process chamber to provide complete liquid removal with minimal bubbling. In a second variation, the lysed moiety-sample solution can be transferred to a vessel that enables the moiety-bound nucleic acid volume to be captured and the waste volume to be removed in a flow through manner, either against the pores of a filter or in the presence of a magnetic field. In the second variation, the microparticles with bound nucleic acids are retained in a filter zone or a magnetic field zone of the vessel, and the liquid portion is flowed into a "waste chamber". In a specific example of the second variation, a system (such as the one described in U.S. patent application Ser. No. 13/766,359, entitled "System and Method for Processing and Detecting Nucleic Acids") can be used to transfer the lysed moiety-sample solution into a fluidic pathway of a cartridge (such as the one described in U.S. patent application Ser. No. 13/765, 996, entitled "Microfluidic Cartridge for Processing and Detecting Nucleic Acids"). In the specific example, the lysed moiety-sample solution can be retained by a magnetic field within a portion of the fluidic pathway upon occlusion of the fluidic pathway at a suitable set of occlusion positions, in order to separate the moiety-bound nucleic acid volume from the waste volume. The waste volume can then be removed by pushing the waste volume to a waste chamber of the cartridge.

Step S150 recites washing the moiety-bound nucleic acid volume, and functions to enable the removal of non-specifically bound moieties and to facilitate a subsequent buffer change in Step S160 by displacing any liquid retained during Step S140. In other steps of the method 100, non-specific binding can occur via electrostatic attraction (e.g., by other negatively charged species), surface adsorption, or any other means; thus, Step S150 can substantially remove a large majority of these non-specifically bound species, especially ones bound to the affinity moieties via means other than electrostatic attraction. Preferably, washing the moiety-bound nucleic acid volume comprises delivering a wash solution to the moiety-bound nucleic acid volume and removing the wash solution and any elements carried in the wash solution; however, washing the moiety-bound nucleic acid volume can alternatively comprise delivering a wash solution through a vessel containing the moiety-bound nucleic acid volume, in order to wash the moiety-bound nucleic acid volume in a flow-through manner. Furthermore, the microparticles of the moiety-bound nucleic acid volume can be agitated to go back into a suspension from a compacted state (e.g., during magnetic capture) or the wash solution can simply be flowed over the microparticles to further remove non-specific moieties and facilitate exchange of buffers. The wash solution preferably has a pH less than 9 and comprises purified water (e.g., Ultrapure water, deionized water) and a suitable buffer (e.g., pH 8.0 Tris buffer), but can alternatively comprise any other suitable component or combination of components for washing the moiety-bound nucleic acid volume, as dependent upon the biological sample type. Furthermore, the wash solution is preferably configured so that the bound target nucleic acid(s) is/are virtually undisturbed during Step S150. Additionally, variations of Step S150 can comprise multiple iterations of washing with the same or a different wash solution for more stringent removal of the non-nucleic acid material (e.g., inhibitors, non-desired elements) as well as facilitating a more thorough buffer exchange.

In a first example of Step S150, the wash solution is delivered through a vessel containing the moiety-bound nucleic acid volume in a continuous flow model. In the first example, the total wash solution volume and flow rate define the efficacy of the washing procedure rather than the number of washing iterations. The flow rate is implemented based upon ensuring that the captured microparticles are not lost but the flow velocity provides adequate agitation to ensure removal of the bound non-target nucleic acid material/inhibitor. In the first example, the total wash solution volume is measured as a multiple of the volume of the vessel containing the captured microparticles or the retained volume of the compacted microparticles of the moiety-bound nucleic acid volume. In the first example, the flow rates are in the range of 1-10 microliters/second, and the total wash solution volume is 50-500 microliters.

In a variation of the first example of Step S150, a system (such as the one described in U.S. patent application Ser. No. 13/766,359, entitled "System and Method for Processing and Detecting Nucleic Acids") can be used to deliver the wash solution into a fluidic pathway of a cartridge (such as the one described in U.S. patent application Ser. No. 13/765,996, entitled "Microfluidic Cartridge for Processing and Detecting Nucleic Acids"). In the variation of the first example, the microparticles of the moiety-bound nucleic acid volume can be retained by a magnetic field within a portion of the fluidic pathway upon occlusion of the fluidic pathway at a suitable set of occlusion positions, and the wash solution can be delivered through the portion of the fluidic pathway and into a waste chamber of the cartridge to wash the microparticles with the bound target nucleic acid(s).

Step S160 recites releasing a nucleic acid sample from the moiety-bound nucleic acid volume, and functions to separate the microparticles from the bound nucleic acid of the moiety-bound nucleic acid volume by using a reagent (i.e., an elution solution) that mitigates the affinity of the coated microparticles for the target nucleic acid(s) and creates an environment for the release of the target nucleic acid(s) from the microparticles. Preferably, Step S160 enables the elution/release of as much of the bound target nucleic acids in the fastest amount of time; however, Step S160 can alternatively or additionally enable the elution/release of as much of the bound target nucleic acids using the smallest volume of elution solution or any other suitable limiting parameter. For example, the target nucleic acid(s) from 0.5 mL of an initial biological sample (undiluted by collection buffer) can be processed using the method 100 and eluted into ~10 uL of elution solution. In other examples, elution solution volumes can be as low as 5 microliters resulting in a significant (50×-100×) concentration of the target nucleic acid from the initial biological sample.

In one variation of Step S160, the affinity moieties, examples of which are described in Section 2 below, function based upon the pH of the environment. Specifically, at low pH, the affinity moieties are positively charged, which results in attraction to negatively charged nucleic acids; however, at high pH, the affinity moieties are negatively charged, which results in repulsion of negatively charged nucleic acids. In a specific example of this variation, releasing the nucleic acid sample comprises providing an elution solution that is in the range of pH 12-pH 13 to effect efficient elution/release of the bound target nucleic acid(s) from the microparticle based upon a shift to a more basic pH. In the specific example, the elution solution comprises 20 mM of NaOH; however, in other variations the elution solution can comprise any other suitable concentration of NaOH or KOH, depending upon the application (e.g., sample type). Again, substantial removal of the wash solution during variations of the method 100 comprising Step S150 can facilitate or enhance the pH-shift for nucleic acid release, as the wash solution can potentially neutralize the elution solution in an undesirable manner and mitigate the elevated pH necessary for releasing the target nucleic acid(s).

In some variations, Step S160 can further comprise Step S161, which recites heating the moiety-bound nucleic acid volume. Step S161 functions to provide additional environmental conditions that facilitate release of the nucleic acid sample from the microparticles, and can further function to mitigate effects of proteolytic enzymes that are used in Steps S110, S120, and/or S130 or that may be released from the biological sample containing the nucleic acid. Preferably, an elevated temperature in combination with an elevated pH resulting from the elution solution provides the enhanced conditions to facilitate the release of the nucleic acid sample. Furthermore, an elevated temperature (e.g., elevating a sample eluted at room temperature to 85 C) can function to minimize protease enzyme activity in the eluted nucleic acid and thereby improve the robustness of the detection of the target nucleic acid sample during processing in variations of Step S110; however, the method 100 can alternatively omit Step S161 in applications wherein heating the moiety-bound nucleic acid volume is undesirable and/or unnecessary. Furthermore, variations of Step S161 can comprise heating at higher temperatures for shorter time periods, or heating at lower temperatures for longer time periods. In an example of Step S161, heating comprises elevating the temperature of the moiety-bound nucleic acid volume to 80-85 C, for 3 minutes, and in another example, heating comprises elevating the temperature of the moiety-bound nucleic acid volume to 50-70 C, for 3-10 minutes. In other examples, the elevation temperature can be maintained at a desired set-point for as low as 1 minute or as high as 30 minutes. Further, elution conditions may be optimized to ensure that the bound nucleic acid is only eluted in the presence of the high pH solution at the elevated temperature for a specified amount of time.

In a specific example of Steps S160 and S161, a system (such as the one described in U.S. patent application Ser. No. 13/766,359, entitled "System and Method for Processing and Detecting Nucleic Acids") can be used to deliver the elution solution into a fluidic pathway of a cartridge (such as the one described in U.S. patent application Ser. No. 13/765,996, entitled "Microfluidic Cartridge for Processing and Detecting Nucleic Acids"). In the variation of the specific example, the microparticles of the moiety-bound nucleic acid volume can be retained by a magnetic field within a portion of the fluidic pathway upon occlusion of the fluidic pathway at a suitable set of occlusion positions, and the elution solution can be delivered through the portion of the fluidic pathway enable release of the nucleic acid sample from the microparticle. Additionally, a heating element of the system can be moved proximal to the portion of the fluidic pathway with the elution solution and the microparticles to further enhance release of the nucleic acid sample.

While the method 100 preferably comprises Steps S150 and S160, other variations of the method 100 can omit Steps S150 and S160. In one variation, Step S150 can be omitted such that release in Step S160 occurs without washing the moiety-bound nucleic acid volume. In another variation, Step S160 can be omitted such that the target nucleic acid(s) bound to microparticles in the moiety-sample volume can be incorporated into a downstream assay without eluting or releasing the target nucleic acid(s) from the microparticle. Other variations of the method 100 can omit steps or rearrange steps according to the specific application.

Furthermore, variations of the method 100 can further comprise Step S165, which recites spiking at least one of the biological sample and the nucleic acid sample with a process control. The process control (e.g., SPC1) preferably comprises a set of primers and probes based upon the type(s) of nucleic acids (e.g., RNA, DNA) in samples being processed, and in a specific example, comprises a set of primers and probes based upon a synthetic DNA strand incorporated into a plasmid or an RNA bacteriophage MS2. In other examples, the process control can be configured to serve as a process control for RNA, DNA, or RNA and DNA in biological samples being processed. The process control can also serve as a monitor for duplex extractions (e.g., duplex PCR in an MS2+*Enterovirus* assay). Furthermore, the process control can be optimized for implementation with multiple matrices.

In Step S165, the process control can be spiked before lysis of the biological sample in variations of Step S120, and/or can be spiked after elution of the nucleic acid sample in variations of Step S160. In variations of the method 100 comprising Step S165, however, the method 100 preferably comprises washing the moiety-bound nucleic acid volume, as in variations of step S150. In specific examples, however, Step S165 can comprise any combination of: not washing the moiety-bound nucleic acid volume, passively washing the moiety-bound nucleic acid volume, not removing a wash solution from the moiety-bound nucleic acid volume, washing the moiety-bound nucleic acid volume with a Tris solution (e.g., 1 mM Tris solution), eluting the nucleic acid sample at room temperature, eluting the nucleic acid sample at 99 C, eluting the nucleic acid sample at 55 C, and not resuspending moiety-bound microparticles in a release buffer, any combination of which can affect amplification of the nucleic acids or the process control.

As shown in FIGS. 1A, 1B, and 2, the method 100 can further comprise Step S170, which recites processing the nucleic acid sample. Processing can comprise amplifying the nucleic acid(s) of the nucleic acid sample (e.g., by polymerase chain reaction), or any other suitable method for processing nucleic acids. In any of the methods for processing nucleic acids, Step S170 can further comprise buffering the nucleic acid sample, for example, to neutralize the pH of the elution solution in Step S160, or combining the nucleic acid sample with nuclease inhibitors (e.g., TCEP, b-mercaptoethanol, DTT, EDTA, SDS, LDS) to facilitate long term storage of the nucleic acid sample. In one variation, the nucleic acid sample eluted from the microparticles can be aspirated (e.g., by a pipette tip or by a fluid handling system) into another process chamber and combined with process reagents for further processing and characterization. In a specific example of this variation, a system (such as the one described in U.S. patent application Ser. No. 13/766,359, entitled "System and Method for Processing and Detecting Nucleic Acids") can be used to aspirate the nucleic acid sample from a fluidic pathway of a cartridge (such as the one described in U.S. patent application Ser. No. 13/765,996, entitled "Microfluidic Cartridge for Processing and Detecting Nucleic Acids"), while the microparticles are immobilized by a magnet. The system can then combine the nucleic acid sample with process reagents (e.g., PCR reagents) in a separate container (e.g., assay plate), and then transfer the nucleic acid sample combined with process reagents to a detection chamber of the fluidic pathway (upon occlusion and/or opening of the fluidic channel at another subset of occlusion positions). The nucleic acid sample combined with process reagents can then be processed within a diagnostic chamber that is coupled to the fluidic pathway.

As a person skilled in the art will recognize from the previous detailed description and from the figures and claims, modifications and changes can be made to the embodiments of the method 100 without departing from the scope of the method 100.

2. Example Affinity Moieties

Nucleic acid molecules are typically negatively charged at standard processing conditions. In such processes, positively charged moieties can capture and retain the negatively charged nucleic acid molecules; however, the positively charged moieties can bind too strongly with target nucleic acids leading to an irreversible process whereby the bound nucleic acid cannot be released into the solution for further processing/analysis. Two novel molecules that are capable of binding nucleic acid in a reversible manner are described below, wherein the reversible binding is modulated by changing the pH of the environment.

2.1 Poly(allylamine)

Poly(allylamine), or PAA, is a cationic polyelectrolyte prepared by the polymerization of allylamine. Allylamine is an organic compound with the formula $C_3H_5NH_2$.

An exemplary PAA molecule has the following formula:

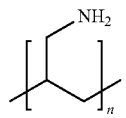

PAA is typically a linear molecule consisting of repeating units of allylamine; however, alternative formulations of PAA may exhibit some branching. In one embodiment of a novel PAA formulation, a wide range of molecular weights of PAA are synthesized and utilized in an embodiment by controlling the extent of polymerization during synthesis of PAA. Due to its strong affinity for nucleic acid, PAA of significantly longer lengths (molecular weights greater than 30,000 Da) can bind to target nucleic acids too strongly resulting in inefficient release of bound target nucleic. Thus, PAA of molecular weights smaller than 30,000 Da are preferable and can be synthesized by controlling the extent of polymerization (e.g., by chain termination reactions, by chain transfer reactions, by chain cleavage reactions). However, strong binding induced by PAA with molecular weights greater than 30,000 Da can be mitigated via the use of stronger elution solutions (e.g., elution solutions with a pH of 14). PAA can act as an inhibitor of enzymatic reactions, due to its strong propensity to bind to nucleic acids and other negatively charged species. Thus, it is preferable that PAA does not reside in solution with the nucleic acid during analysis, for example, during processing of the nucleic acid sample in Step S170 as described in Section 1 above.

2.2 Polypropylenimine Tetramine Dendrimer

Polypropylenimine tetramine dendrimer Generation 1, or DABAM Generation 1, is a cationic polyelectrolyte dendrimer. Dendrimers are repetitively branched molecules. A dendrimer is typically symmetric around a core, and often adopts a spherical three-dimensional structure.

An exemplary DABAM molecule has the following formula:

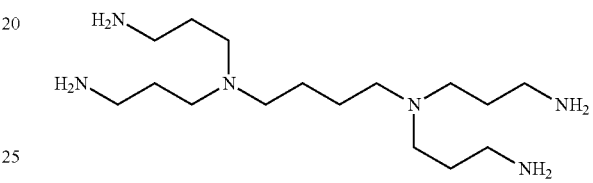

DABAM is typically a linear molecule with the formula [—CH2 CH2N(CH2 CH2 CH2NH2)2]2. The example embodiments of DABAM suitable for use in the methods described herein are synthesized and utilized in one variation by controlling the dendrimer formation during synthesis. Due to its strong affinity for nucleic acids, DABAM of significantly higher generations (e.g., beyond Generation 2) may bind the nucleic acid too strongly resulting in inefficient release of bound nucleic acids. Thus, DABAM of generation less than 2 are preferable and can be synthesized by controlling the extent of dendrimer polymerization (e.g., by chain termination reactions, by chain transfer reactions, by chain cleavage reactions). However, strong binding induced by DABAM of generation greater than or equal to 2 can be mitigated via the use of stronger elution solutions (e.g., elution solutions with a pH of 14). In addition, DABAM can act as an inhibitor of enzymatic reactions, due to its strong propensity to bind to nucleic acids and other negatively charged species. Thus, it is preferable that be DABAM does not reside in solution with the nucleic acid during analysis, for example, during processing of the nucleic acid sample in Step S170 as described in Section 1 above.

2.3 Support Materials

The affinity moieties, such as the PAA and DABAM described in Section 2.1 and 2.2, can be immobilized on a suitable substrate to facilitate subsequent capture of target nucleic acids bound to the substrate (e.g., by magnetic separation, size-based separation, density-based separation, or focusing). A process for coupling the affinity moiety to the substrate preferably relies on creation of a covalent bond between the affinity moiety and the microparticle, and in one variation as described below, a carboxylic acid group (—COOH) can be used to form the covalent bond between the microparticles and the affinity moieties.

Figure 3:
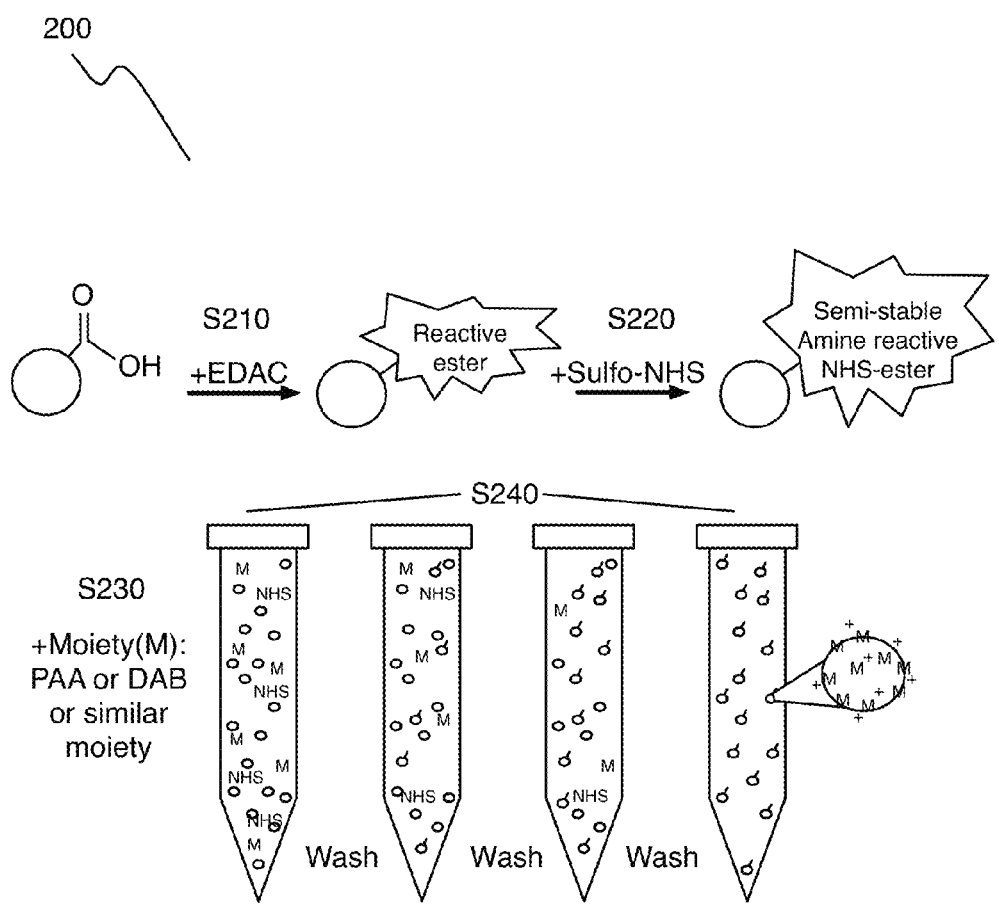
FIG. 3 is a schematic representation of an embodiment of a method for bonding microparticles with an affinity moiety useful for isolation of nucleic acid materials.

As shown in FIG. 3, a method 200 for coupling the microparticles with the affinity moieties comprises activating carboxylated microparticles with EDAC 5210 to form a set of microparticle-reactive ester compounds; treating the set of microparticle-reactive ester compounds with an N-Hydroxysuccinimide to form a set of microparticle-amine reactive ester compounds S220, combining the set of microparticle-amine reactive ester compounds with a set of affinity moieties selected from the group comprising PAA and DABAM S230 to produce a microparticle-moiety solution; and washing the microparticle-moiety solution, thereby producing a set of microparticles covalently bonded to the set of affinity moieties by amide bonds S240. The method 200 functions to produce a set of moiety-bound microparticles for nucleic acid isolation. Preferably, the microparticles are magnetic to facilitate nucleic acid isolation by magnetic separation; however, the microparticles can alternatively be characterized by any suitable feature that facilitates nucleic acid isolation, as described earlier in Section 1.

In a specific example, as shown in FIG. 3, the method 200 comprises activating magnetic carboxylated microparticles with EDAC in Step S110 to form a set of magnetic microparticle-reactive ester compounds; treating the set of magnetic microparticle-reactive ester compounds with a N-Hydroxysulfosuccinimide to form a set of microparticle-amine reactive ester compounds S220; combining the set of microparticle-amine reactive ester compounds with a set of affinity moieties selected from the group comprising PAA of molecular weight less than 30,000 Da and DABAM of generation less than two S230 to produce a microparticle-moiety solution; and repeatedly washing the microparticle-moiety solution, thereby producing a set of magnetic microparticles covalently bonded to the set of affinity moieties by amide bonds S240.

Other variations and examples of the method 200 can comprise performing steps of the method 200 simultaneously and/or in any suitable order, and using any suitable alternative components for forming bonds between the microparticles and the affinity moieties.

3. Representative Examples and Results of the Method

Sections 3.1-3.17 describe representative examples of methods of DNA and RNA isolation from multiple sources. Specific reagents used in the representative examples, including binding moiety solutions, wash solutions, and elution solutions, are described in Section 4 below.

3.1 Representative RNA Isolation Method and Results: Example 1

Figure 4:
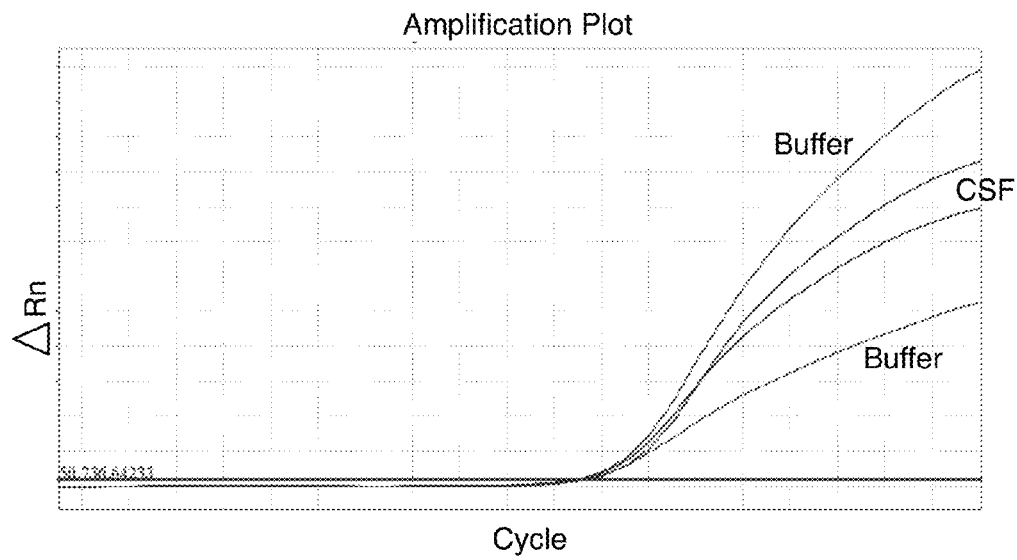
FIG. 4 shows the performance of example nucleic acid isolation reagents for the extraction of *Enterovirus* RNA target from cerebrospinal fluid specimen using a real-time RT-PCR assay.

A first example of the method 100 comprises using PAA affinity moieties coated onto magnetic microparticles, cerebrospinal fluid (CSF) as a representative biological sample, and *Enterovirus* (EV) viral particles as the model target. In the first example, 200 μL of CSF was spiked with 2 uL of EV viral particle lysate and then mixed with 500 μL of RNA Collection Buffer 1 (CBR-1) and 300 μL of nuclease-free water in examples of Steps S110 and S120. As a comparison, a similar amount of EV particle lysate was spiked into a 1 mL solution comprised of 500 μL of CBR-1 buffer and 500 μL of nuclease-free water and processed simultaneously. In an example of Step S130, RNA was allowed to bind to the PAA affinity moieties coated onto magnetic microparticles for 10 minutes at 60 C. Upon removal of the unbound supernatant in an example of Step S140, the magnetic microparticles with bound RNA were washed twice (2x) with 500 μL of WSH-1 solution in an example of Step S150 and the captured RNA was eluted from the affinity matrix by using ELU-2 at 85 C for 3 minutes in an example of Step S160. Isolated RNA was eluted into 10 μL of ELU-2 and 8 μL of the eluate was used for real-time RT-PCR in an example of Step S170. As shown in FIG. 4, results of the RNA isolation as elucidated by a real-time *Enterovirus* RT-PCR assay indicate that the RNA isolation process is substantially equally efficient in the biological sample matrix as compared to a simple buffer sample. This indicates that the example method 100 and the nucleic acid isolation reagents are efficacious at capture, release and cleanup of the target RNA in CSF matrix in the first example.

3.2 Representative RNA Isolation Method and Results: Example 2

Figure 5:
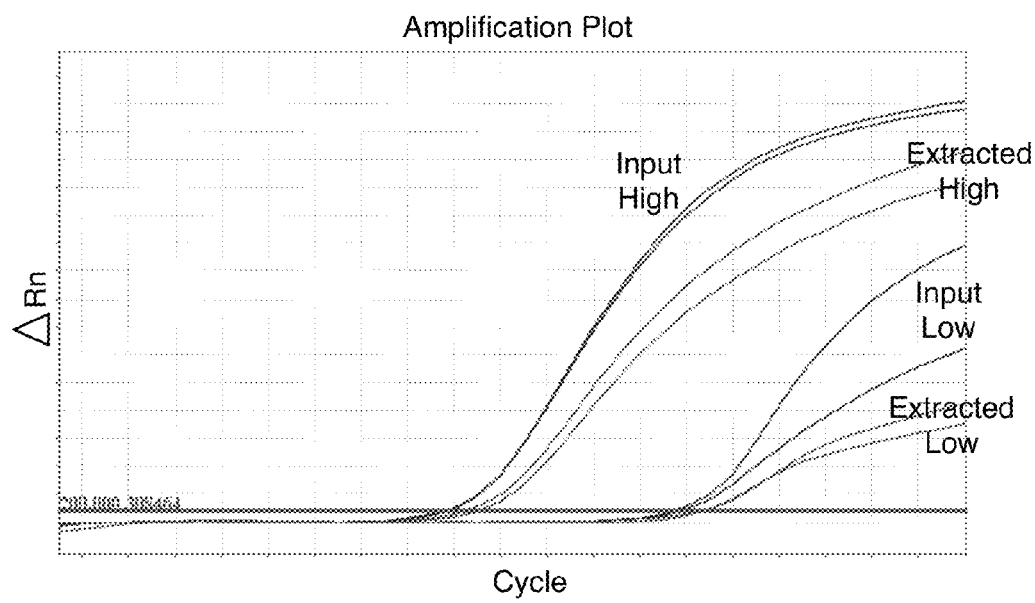
FIG. 5 shows the performance of example nucleic acid isolation reagents for the extraction of *Enterovirus* RNA target from M4 transport medium using a real-time RT-PCR assay.

A second example of the method 100 comprises using PAA affinity moieties coated onto magnetic microparticles, M4 transport medium containing a nasal swab (donor) as a representative biological sample, and *Enterovirus* (EV) viral particles as the model target. In the second example, 500 μL of M4 transport media containing a nasal swab (donor) was spiked with 2 μL of either a $10^{-2}$ dilution (high) or a $10^{-4}$ (low) dilution of EV RNA (purified from 200 μL viral particle lysate and eluted in 20 μL total volume) and then mixed with 500 μL of RNA Collection Buffer 1 (CBR-1) and 0.4 mg of Proteinase K in examples of Steps S110 and S120. RNA was allowed to bind to the PAA affinity moieties coated onto magnetic microparticles for 10 minutes at 60 C in an example of Step S130. Upon removal of the unbound supernatant in an example of Step S140, the magnetic microparticles with bound RNA were washed twice (2x) with 250 μL of WSH-1 solution in an example of Step S150, and the captured RNA was eluted from the affinity matrix by using ELU-2 at 85 C for 3 minutes in an example of Step S160. RNA was then eluted into 10 μL of ELU-2 and 8 μL of the eluate was used for real-time RT-PCR in an example of Step S170. As a comparison, a similar amount of EV RNA was used directly in real-time RT-PCR at both low and high input levels as a reference, which would correlate to an extraction efficiency of 100%. As shown in FIG. 5, results of the RNA isolation as elucidated by a real-time *Enterovirus* RT-PCR assay indicate that the RNA isolation process is efficient in the biological sample matrix as compared to the input PCR control samples that were not subject to the full extraction process. A small shift in the amplification of the extracted samples does not necessarily indicate a loss in extraction efficiency or sensitivity. This indicates that the example method 100 and the nucleic acid isolation reagents are efficacious at capture, release and cleanup of the target RNA in M4 transport media matrix.

3.3 Representative RNA Isolation Method and Results: Example 3

Figure 6:
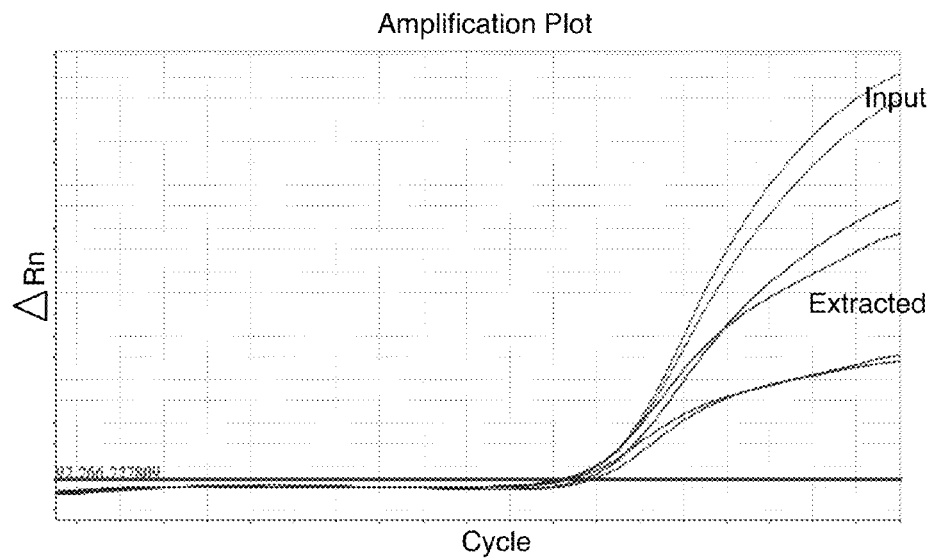
FIG. 6 shows the performance of the example nucleic acid isolation reagents for the extraction of *Enterovirus* RNA target from UTM (Universal Transport Media) using a real-time RT-PCR assay.

A third example of the method 100 comprises using PAA affinity moieties coated onto magnetic microparticles, Universal Transport Medium (UTM) containing a nasal swab (donor) as a representative biological sample, and *Enterovirus* (EV) viral particles as the model target. In the third example, 500 μL of UTM transport media containing a nasal swab (donor) was spiked with 2 μL of a $10^{-4}$ dilution of EV RNA (purified from 200 μL viral particle lysate and eluted in 20 μL total volume) and then mixed with 500 μL of RNA Collection Buffer 1 (CBR-1) and 0.6 mg of Proteinase K in examples of Steps S110 and S120. RNA was allowed to bind to the PAA affinity particles coated onto magnetic microparticles for 10 minutes at 60 C in an example of Step S130. Upon removal of the unbound supernatant in an example of Step S140, the magnetic microparticles with bound RNA were washed twice (2x) with 100 μL or 250 μL of WSH-1 solution in an example of Step S150 and the captured RNA was eluted from the affinity matrix by using ELU-2 at 85 C for 3 minutes in an example of Step S160. RNA was eluted into 10 μL of ELU-2 and 8 μL of the eluate was used for real-time RT-PCR in an example of Step 170. As a comparison, a similar amount of EV RNA was used directly in real-time RT-PCR as a reference, which would correlate to an extraction efficiency of 100%. As shown in FIG. 6, results of the RNA isolation as elucidated by a real-time *Enterovirus* RT-PCR assay indicate that the RNA isolation process is efficient in the biological sample matrix as compared to the input PCR control samples that were not subject to the full extraction process. This indicates that the example method 100 and the nucleic acid isolation reagents are efficacious at capture, release and cleanup of the target RNA in UTM transport media matrix.

3.4 Representative RNA Isolation Method and Results: Example 4

Figure 7:
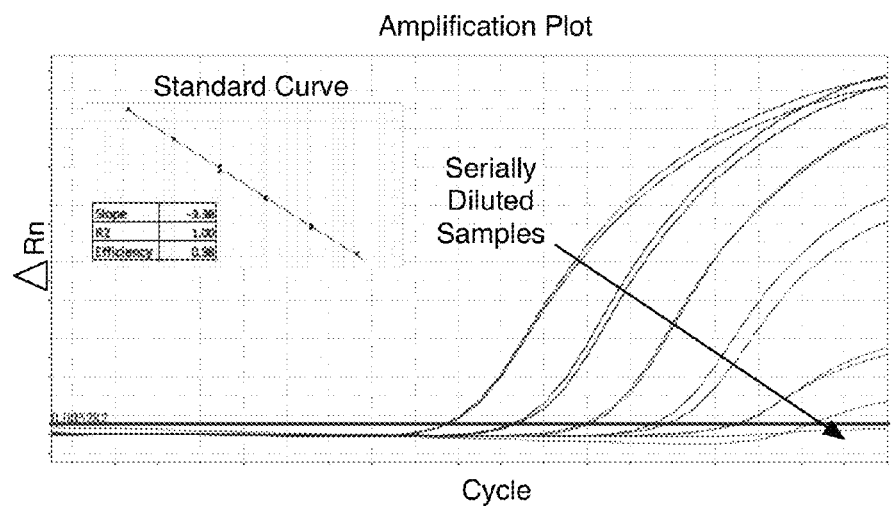
FIG. 7 shows the quantitative performance of the example nucleic acid isolation reagents for the extraction of *Enterovirus* RNA target from a nasal swab transferred to UTM transport medium using a real-time RT-PCR assay.

A fourth example of the method 100 comprises using PAA affinity moieties coated onto magnetic microparticles, M4 transport medium containing nasal swab (donor) as a representative biological sample, and *Enterovirus* (EV) viral particles as the model target. In the fourth example, 500 μL of M4 transport media containing a nasal swab (donor) was spiked with 2 μL of ten-fold dilutions of EV viral particle lysate and then mixed with 500 μL of RNA Collection Buffer 1 (CBR-1) and 0.4 mg of Proteinase K in examples of Steps S110 and S120. RNA was allowed to bind to the PAA affinity moieties coated onto magnetic microparticles for 10 minutes at 60 C in an example of Step S130. Upon removal of the unbound supernatant in an example of Step S140, the magnetic microparticles with bound RNA were washed twice (2×) with 100 μL of WSH-1 solution in an example of Step S150, and the captured RNA was eluted from the affinity matrix by using ELU-2 at 85 C for 3 minutes in an example of Step S160. RNA was eluted into 10 μL of ELU-2 and 2 μL of the eluate was used for real-time RT-PCR in an example of Step S170. As shown in FIG. 7, results of the RNA isolation as elucidated by a real-time *Enterovirus* RT-PCR assay indicate that the RNA isolation process is efficient in the biological sample matrix as demonstrated by the standard curve generated from the RT-PCR Ct values obtained from the serially-diluted extracted samples. This indicates that the example method 100 and the nucleic acid extraction process of RNA in UTM transport media is both efficient and sensitive, with a broad dynamic range.

In other variations of the first through fourth examples involving RNA extractions, the example method 100 can comprise any suitable combination of: adding guanidine to an RNA lysis buffer (e.g., 50 mM GuSCN), adding guanidine to a swab extraction buffer (e.g., 2M GuHCL, 2.5M GuHCL), providing any suitable lysis buffer (e.g., 50 mM TRIS pH 7 with 1% Triton X, 50 mM EDTA, and 2M GuHCL; 1 mM Tris pH 8 in 1% Triton X and 100 mM EDTA), binding RNA to affinity moiety-coated microparticles at any suitable temperature (e.g., 37-60 C for up to 10 minutes), using any suitable amount (e.g., 7.5 ug) of tRNA during lysis, using fresh or frozen samples, providing any suitable wash conditions (e.g, 1× salt wash, 1× salt wash+1× 1 mM TRIS pH 8 wash), providing any suitable binding conditions (e.g., 2× 1 mM TRIS pH 8 binding at 37 C, 2× 1 mM TRIS pH 8 at 60 C), eluting with any suitable elution conditions (e.g., room temperature to 85 C, 1 minute-10 minutes), providing any suitable composition of an elution solution (e.g., 20 mM NaOH, 40 mM NaOH, KOH), and using any suitable PCR mix for EV extractions.

3.5 Representative DNA Isolation Method and Results: Example 5

Figures 8, 9:
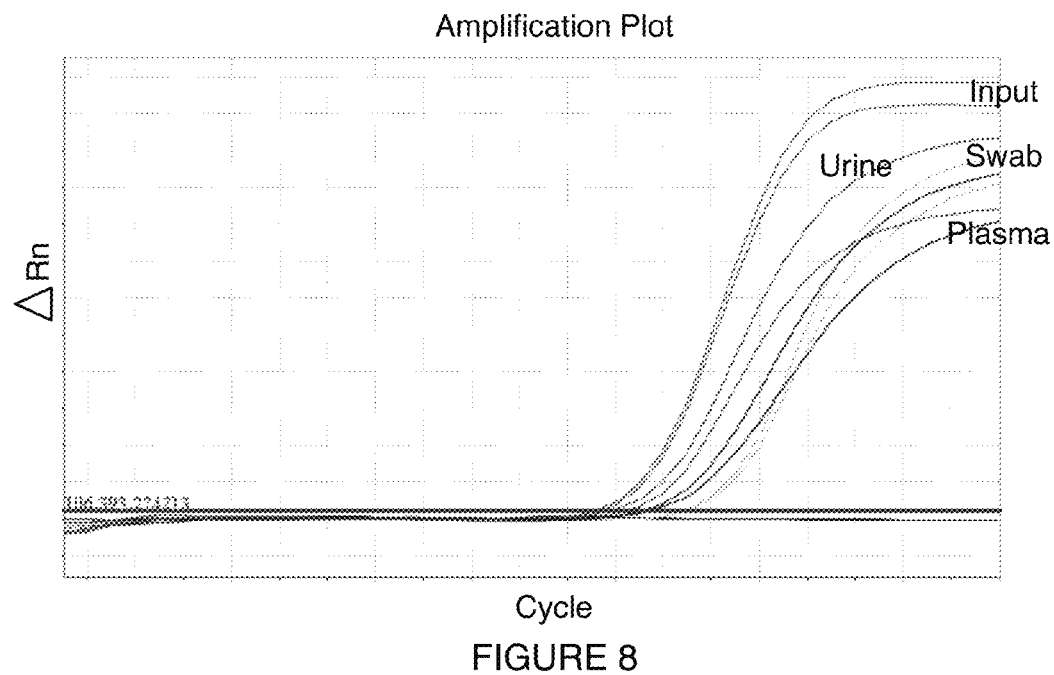
FIG. 8 demonstrates the use of nucleic acid isolation reagents and an embodiment of a process to isolate and purify Group B *Streptococcus* DNA using DAB affinity particles, in a variety of biological samples (clinical matrices) for subsequent real-time PCR assay implementation.
FIG. 9 demonstrates the use of nucleic acid isolation reagents and an embodiment of a process to isolate and purify Group B *Streptococcus* DNA using PAA affinity particles, in Human Urine specimens, for subsequent real-time PCR assay implementation.

A fifth example of the method 100 comprises using DABAM affinity moieties coated onto magnetic microparticles, Human Urine (donor), Human Plasma and Buccal Swab (donor) as representative biological sample matrices, and Group B *Streptococcus* (GBS) DNA (ATCC, Virginia) as the model target. In the fifth example, 500 μL of Urine or Plasma was spiked with 10 pg of GBS DNA and then mixed with 500 μL of DNA Collection Buffer 2 (CBD-2) in examples of Steps S110 and S120. Alternately, a buccal swab was added to 1 mL of DNA Collection Buffer 1 (CBD-1) containing 0.4 mg Proteinase K and then spiked with 10 pg of GBS DNA in other examples of Steps S110 and S120. DNA was allowed to bind to the DABAM affinity moieties coated onto magnetic microparticles for 10 minutes at room temperature or 60 C depending on matrix used in examples of Step S130. Upon removal of the unbound supernatant in an example of Step S140, the magnetic microparticles with bound DNA were washed with 500 μL of WSH-1 solution in an example of Step S150, and the captured DNA was eluted from the affinity matrix by using ELU-1 and heating the microparticles to 85 C for 3 minutes in an example of Step S160. DNA was eluted into 10 μL of ELU-1 and 8 μL of the eluate was used for real-time PCR in an example of Step S170. As a comparison, a similar amount of GBS DNA was used directly in real-time PCR as a reference, which would correlate to an extraction efficiency of 100%. As shown in FIG. 8, results of the DNA isolation as elucidated by a GBS real-time PCR assay indicate that the DNA isolation process is efficient in the biological sample matrices as compared to the input PCR control samples that were not subject to the full extraction process. A small shift in the amplification of the extracted samples does not necessarily indicate a loss in extraction efficiency or sensitivity. This indicates that the example method 100 and nucleic acid isolation reagents are efficacious at capture, release and cleanup of the target DNA in Urine, Plasma, and Swab matrices.

3.6 Representative DNA Isolation Method and Results: Example 6

A sixth example of the method 100 comprises using PAA affinity moieties coated onto magnetic microparticles, Human Urine (donor) as a representative biological sample, and Group B *Streptococcus* (GBS) DNA as the model target. In the sixth example, 500 μL of Urine (obtained from donor) was spiked with mpg of GBS DNA and then mixed with 500 μL of DNA Collection Buffer 2 (CBD-2) in examples of Steps S110 and S120. DNA was allowed to bind to the PAA affinity moieties coated onto magnetic microparticles for 10 minutes at room temperature in an example of Step S130. Upon removal of the unbound supernatant in an example of Step S140, the magnetic microparticles with bound DNA were washed with 500 μL of WSH-1 solution in an example of Step S150 and the captured DNA was eluted from the affinity matrix by using ELU-2 and heating the microparticles to 85 C for 3 minutes in an example of Step S160. DNA was eluted into 10 μL of ELU-2 and 2 μL of the eluate was used for real-time PCR in an example of Step S170. As a comparison, a similar amount of GBS DNA was used directly in real-time PCR as a reference which would correlate to an extraction efficiency of 100%. As shown in FIG. 9, results of the DNA isolation as elucidated by a GBS real-time PCR assay indicate that the DNA isolation process is efficient in the biological sample matrix as compared to the input PCR control sample that was not subjected to the full extraction process. A small shift in the amplification of the extracted samples does not necessarily indicate a loss in extraction efficiency or sensitivity. This indicates that the example method 100 and nucleic acid isolation reagents are efficacious at capture, release and cleanup of the target DNA in urine matrix.

3.7 Representative DNA Isolation Method and Results: Example 7

Figure 10:
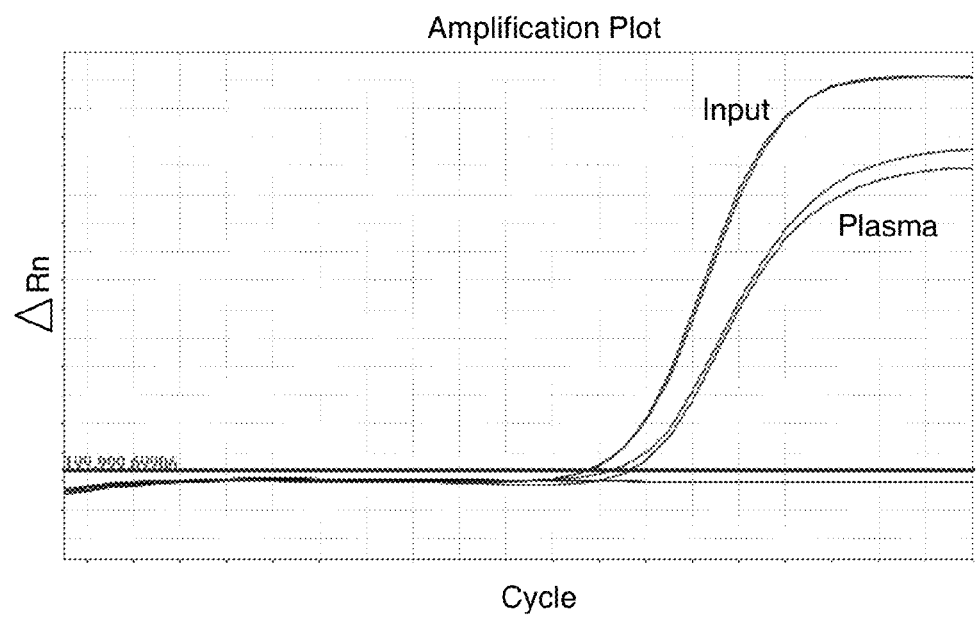
FIG. 10 demonstrates the use of nucleic acid isolation reagents and an embodiment of a process to isolate and purify Group B *Streptococcus* DNA using PAA affinity particles, in Human Plasma specimens, for subsequent real-time PCR assay implementation.

A seventh example of the method 100 comprises using PAA affinity moieties coated onto magnetic microparticles, Human Plasma (donor, obtained from Bioreclamation, Inc.) as a representative biological sample, and Group B *Streptococcus* (GBS) DNA as the model target. In the seventh example, 500 μL of Plasma was spiked with mpg of GBS DNA and then mixed with 500 μL of DNA Collection Buffer 2 (CBD-2) in examples of Steps S110 and S120. DNA was allowed to bind to the PAA affinity moieties coated onto magnetic microparticles for 10 minutes at room temperature in an example of Step S130. Upon removal of the unbound supernatant in an example of Step S140, the magnetic microparticles with bound DNA were washed with 500 µL of WSH-1 solution in an example of Step S150 and the captured DNA was eluted from the affinity matrix by using ELU-2 and heating the magnetic microparticles to 85 C for 3 minutes in an example of Step S160. DNA was eluted into 10 µL of ELU-2 and 2 µL of the eluate was used for real-time PCR in an example of Step S170. As a comparison, a similar amount of GBS DNA was used directly in real-time PCR as a reference, which would correlate to an extraction efficiency of 100%. As shown in FIG. 10, results of the DNA isolation as elucidated by a GBS real-time PCR assay indicate that the DNA isolation process is efficient in the biological sample matrix as compared to the input PCR control sample that was not subjected to the full extraction process. A small shift in the amplification of the extracted samples does not necessarily indicate a loss in extraction efficiency or sensitivity. This indicates that the example method 100 and nucleic acid isolation reagents are efficacious at capture, release and cleanup of the target DNA in plasma matrix.

3.8 Representative DNA Isolation Method and Results: Example 8

Figure 11:
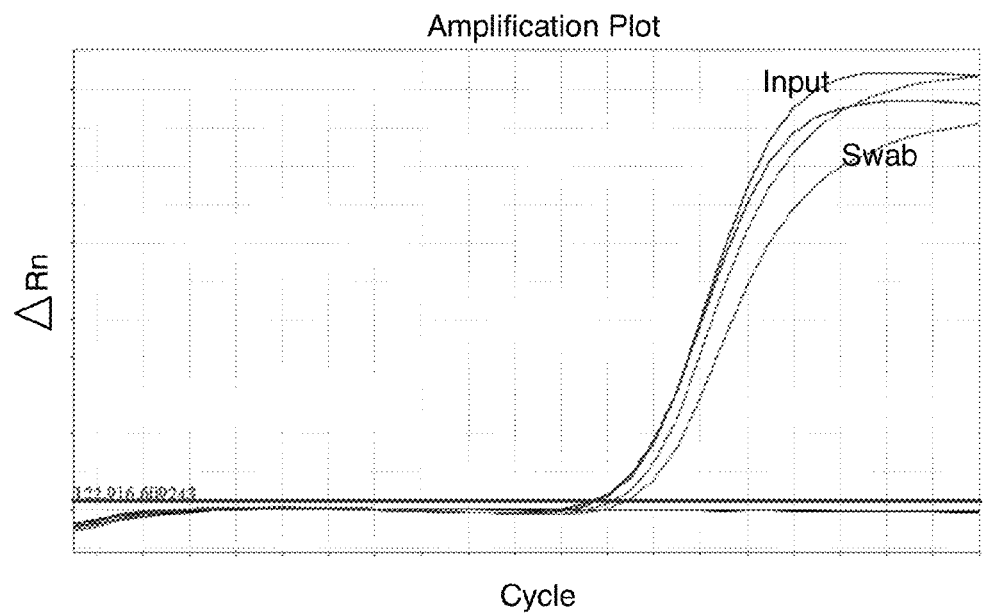
FIG. 11 demonstrates the use of nucleic acid isolation reagents and an embodiment of a process to isolate and purify Group B *Streptococcus* DNA using PAA affinity particles, in simulated swab specimens, for subsequent real-time PCR assay implementation.

An eighth example of the method 100 comprises using PAA affinity moieties coated onto magnetic microparticles, simulated swab specimens as a representative biological sample and Group B *Streptococcus* (GBS) DNA as the model target. In the eighth example, a buccal swab (obtained from a donor) was added to 1 mL of DNA Collection Buffer 1 (CBD-1) containing 0.4 mg Proteinase K and then spiked with 10 pg of GBS DNA in examples of Steps S110 and S120. DNA was allowed to bind to the PAA affinity moieties coated onto magnetic microparticles for 10 minutes at 37 C in an example of Step S130. Upon removal of the unbound supernatant in an example of Step S140, the magnetic microparticles with bound DNA were washed with 500 µL of WSH-1 solution in an example of Step S150, and the captured DNA was eluted from the affinity matrix by using ELU-2 and heating the microparticles to 85 C for 3 minutes in an example of Step S160. DNA was eluted into 10 µL of ELU-2 and 2 µL of the eluate was used for real-time PCR in an example of Step S170. As a comparison, a similar amount of GBS DNA was used directly in real-time PCR as a reference, which would correlate to an extraction efficiency of 100%. As shown in FIG. 11, results of the DNA isolation as elucidated by a GBS real-time PCR assay indicate that the DNA isolation process is efficient in the biological sample matrix as compared to the input PCR control sample that was not subjected to the full extraction process. A small shift in the amplification of the extracted samples does not necessarily indicate a loss in extraction efficiency or sensitivity. This indicates that the example method 100 and nucleic acid isolation reagents are efficacious at capture, release and cleanup of the target DNA in a simulated swab matrix.

3.9 Representative DNA Isolation Method and Results: Example 9

Figure 12:
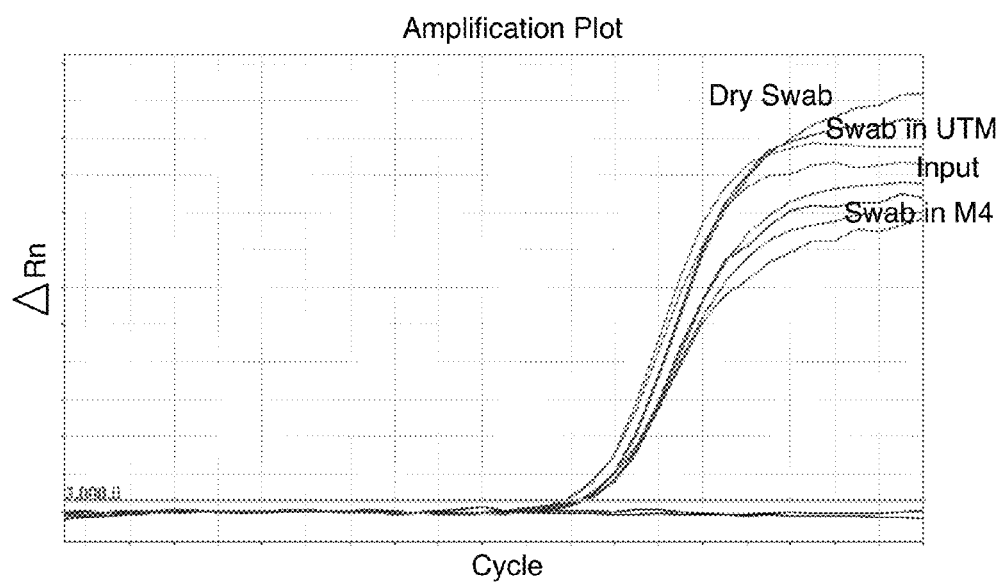
FIG. 12 demonstrates the use of nucleic acid isolation reagents and an embodiment of a process to isolate and purify Group B *Streptococcus* DNA using PAA affinity particles, in simulated swab transport media specimen, for subsequent real-time PCR assay implementation.

A ninth example of the method 100 comprises using PAA affinity moieties coated onto magnetic microparticles, simulated swab transport media specimens as representative biological samples and Group B *Streptococcus* (GBS) DNA as the model target. In the ninth example 500 µL of M4 Transport Media (M4) or Universal Transport Media (UTM) containing a buccal swab (obtained from a donor) was spiked with 10 pg of GBS DNA and then mixed with 500 µL of DNA Collection Buffer 3 (CBD-3) and 0.4 mg of Proteinase K in examples of Steps S110 and S120. For comparison, "Dry Swab" samples were prepared by adding a buccal swab to 1 mL of DNA Collection Buffer 1 (CBD-1) containing 0.4 mg Proteinase K and then spiked with 10 pg of GBS DNA. DNA was allowed to bind to the PAA affinity moieties coated onto magnetic microparticles for 10 minutes at 37 C in an example of Step S130. Upon removal of the unbound supernatant in an example of Step S140, the magnetic microparticles with bound DNA were washed with 500 µL of WSH-1 solution in an example of Step S150 and the captured DNA was eluted from the affinity matrix by using ELU-2 and heating the microparticles to 85 C for 3 minutes in an example of Step S160. DNA was eluted into 10 µL of ELU-2 and 2 µL of the eluate was used for real-time PCR in an example of Step S170. As a comparison, a similar amount of GBS DNA was used directly in real-time PCR as a reference, which would correlate to an extraction efficiency of 100%. As shown in FIG. 12, results of the DNA isolation as elucidated by a GBS real-time PCR assay indicate that the DNA isolation process is efficient in the biological sample matrices as compared to the input PCR control sample that was not subjected to the full extraction process. A small shift in the amplification of the extracted samples does not necessarily indicate a loss in extraction efficiency or sensitivity. This indicates that the example method 100 and nucleic acid isolation reagents are efficacious at capture, release and cleanup of the target DNA in simulated swab transport media matrices.

3.10 Representative DNA Isolation Method and Results: Example 10

Figure 13:
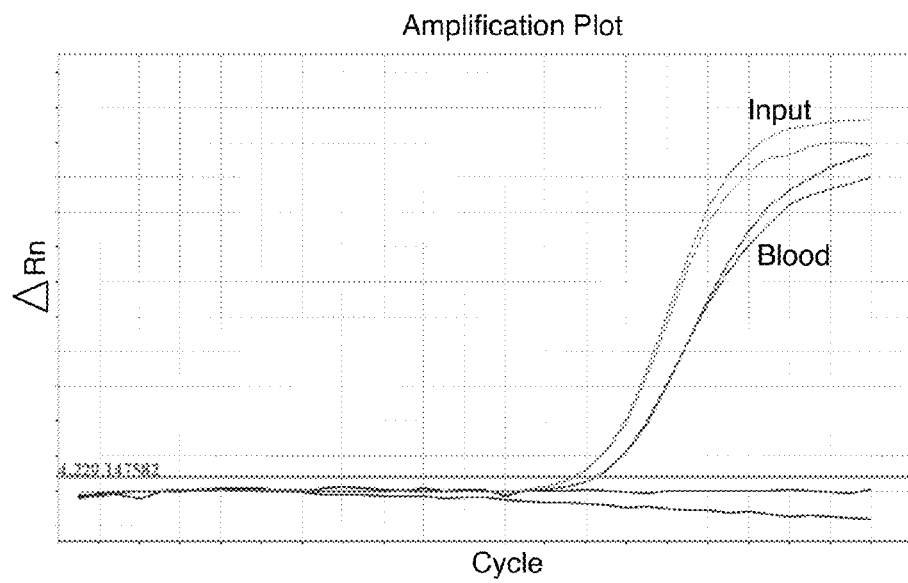
FIG. 13 demonstrates the use of nucleic acid isolation reagents and an embodiment of a process to isolate and purify Group B *Streptococcus* DNA using PAA affinity particles, in Whole Blood specimens (donor), for subsequent real-time PCR assay implementation.

A tenth example of the method 100 comprises using PAA affinity moieties coated onto magnetic microparticles, whole blood as a representative biological sample and Group B *Streptococcus* (GBS) DNA as the model target. In the tenth example, 100 µL whole blood (donor, obtained from Bioreclamation, Inc.) was added to 1 mL of DNA Collection Buffer 1 (CBD-1) containing 0.4 mg Proteinase K and then spiked with 10 pg of GBS DNA in examples of Steps S110 and S120. DNA was allowed to bind to the PAA affinity moieties coated onto magnetic microparticles for 10 minutes at 37 C in an example of Step S130. Upon removal of the unbound supernatant in an example of Step S140, the magnetic microparticles with bound DNA were washed twice with 500 µL of WSH-1 solution in an example of Step S150, and the captured DNA was eluted from the affinity matrix by using ELU-2 and heating the microparticles to 85 C for 3 minutes in an example of Step S160. DNA was eluted into 251 µL of ELU-2 and 81 µL of the eluate was used for real-time PCR in an example of Step S170. As a comparison, a similar amount of GBS DNA was used directly in real-time PCR as a reference which would correlate to an extraction efficiency of 100%. As shown in FIG. 13, results of the DNA isolation as elucidated by a GBS real-time PCR assay indicate that the DNA isolation process is efficient in the biological sample matrix as compared to the input PCR control sample that was not subjected to the full extraction process. A small shift in the amplification of the extracted samples does not necessarily indicate a loss in extraction efficiency or sensitivity. This indicates that the example method 100 and nucleic acid isolation reagents are efficacious at capture, release and cleanup of the target DNA in a whole blood matrix.

In other variations of the tenth example, the example method 100 can comprise any suitable combination of: proteinase K pre-lysis with any suitable concentration of NaCl (e.g., 200 mM, 500 mM, 750 mM, 1M), providing a lysis buffer with any suitable concentration of EDTA and/or TRIS (e.g., 50 mM TRIS, 50 mM EDTA), providing a lysis solution with any suitable amount of Proteinase K (e.g., +/−20-40 uL of 20 mg/mL Proteinase K), any other suitable amount of blood sample (e.g., 10 uL, 25 uL, 50 uL, 100 uL, 250 uL, 500 uL), any other suitable concentration of NaOH (e.g., 20 mM, 40 mM) in an elution solution, any suitable amount (e.g., 30-45 uL) of PAA affinity moieties coated onto microparticles, filtration of blood sample, any suitable number of washing stages (e.g., 1 wash, 2 washes), and freezing and/or thawing of the blood sample.

3.11 Representative DNA Isolation Method and Results: Example 11

Figure 14:
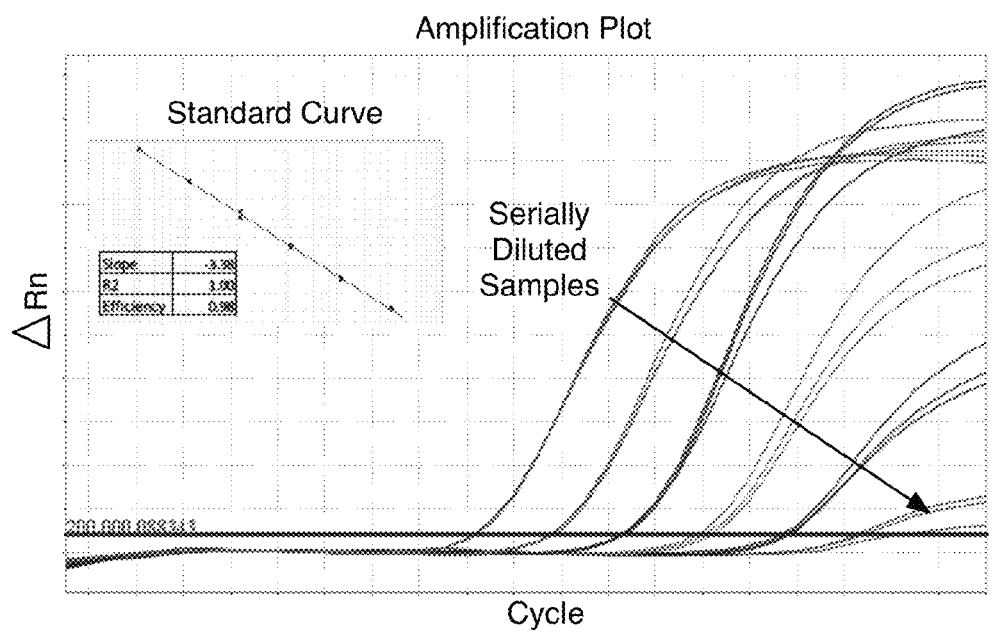
FIG. 14 demonstrates the use of nucleic acid isolation reagents and an embodiment of a process to isolate and purify Group B *Streptococcus* DNA using PAA affinity particles, in Human Urine specimens (donor), for subsequent quantitative real-time PCR assay implementation.

An eleventh example of the method 100 comprises using PAA affinity moieties coated onto magnetic microparticles, Urine (donor) as a representative biological sample and Group B *Streptococcus* (GBS) DNA as the model target. In the eleventh example, 500 μL of urine (obtained from a donor) was spiked with ten-fold serial dilutions of GBS DNA from 1 ng to 10 fg and then mixed with 500 μL of DNA Collection Buffer 2 (CBR-2) in examples of Steps S110 and S120. DNA was allowed to bind to the PAA affinity moieties coated onto magnetic microparticles for 10 minutes at room temperature in an example of Step S130. Upon removal of the unbound supernatant in an example of Step S140, the magnetic microparticles with bound DNA were washed with 500 μL of WSH-1 solution in an example of Step S150, and the captured DNA was eluted from the affinity matrix by using ELU-2 at 85 C for 3 minutes in an example of Step S160. DNA was eluted into 10 μL of ELU-2 and 2 μL of the eluate was used for real-time PCR in an example of Step S170. As shown in FIG. 14, results of the DNA isolation as elucidated by a real-time GBS PCR assay indicate that the DNA isolation process is efficient in the biological sample matrix as demonstrated by the standard curve generated from the PCR Ct values obtained from the serially-diluted extracted samples. This indicates that the example method 100 and nucleic acid extraction process of DNA in a urine matrix is both efficient and sensitive, with a broad dynamic range.

In other variations of the eleventh example, the example method 100 can comprise any suitable combination of: providing a lysis solution with any suitable amount of Proteinase K (e.g., 20-40 uL of 20 mg/mL Proteinase K) and providing any suitable wash solution (e.g., 1 mM TRIS pH, 150 mM NaCL).

3.12 Representative DNA Isolation Method and Results: Example 12

Figure 15:
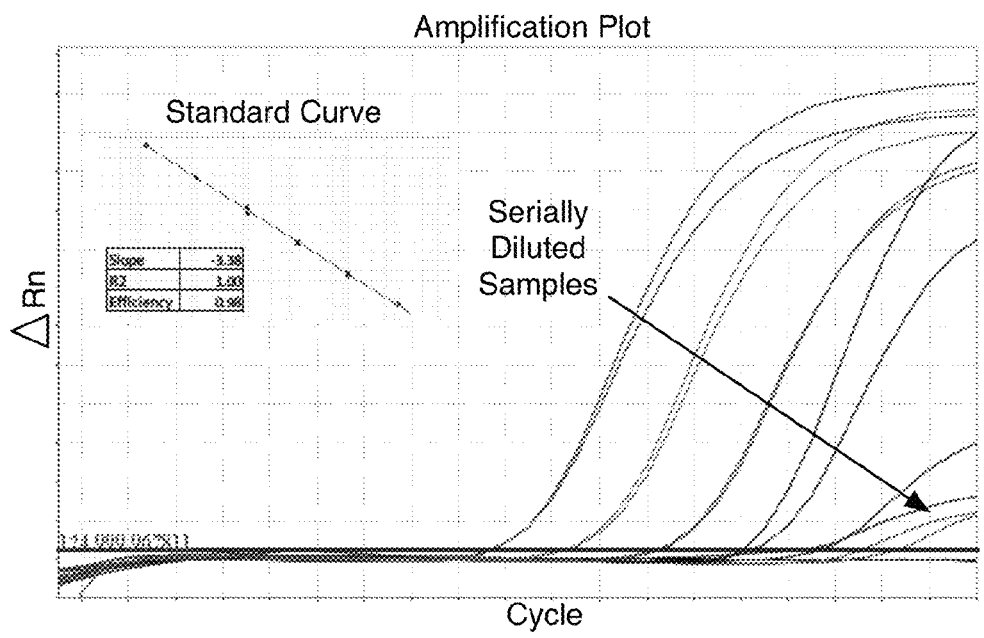
FIG. 15 demonstrates the use of nucleic acid isolation reagents and an embodiment of a process to isolate and purify Group B *Streptococcus* DNA using PAA affinity particles, in Human Plasma specimens (donor), for subsequent quantitative real-time PCR assay implementation.

A twelfth example of the method 100 comprises using PAA affinity moieties coated onto magnetic microparticles, plasma (donor) as a representative biological sample, and Group B *Streptococcus* (GBS) DNA as the model target. In the twelfth example, 500 μL of plasma was spiked with ten-fold serial dilutions of GBS DNA from 1 ng to 10 fg and then mixed with 500 μL of DNA Collection Buffer 2 (CBR-2) in examples of Steps S110 and S120. DNA was allowed to bind to the PAA affinity moieties coated onto magnetic microparticles for 10 minutes at room temperature in an example of Step S130. Upon removal of the unbound supernatant in an example of Step S140, the magnetic microparticles with bound DNA were washed with 500 μL of WSH-1 solution in an example of Step S150, and the captured DNA was eluted from the affinity matrix by using ELU-2 at 85 C for 3 minutes in an example of Step S160. DNA was eluted into 10 μL of ELU-2 and 2 μL of the eluate was used for real-time PCR in an example of Step S170. As shown in FIG. 15, results of the DNA isolation as elucidated by a real-time GBS PCR assay indicate that the DNA isolation process is efficient in the biological sample matrix as demonstrated by the standard curve generated from the PCR Ct values obtained from the serially-diluted extracted samples. This indicates that the example method 100 and nucleic acid extraction process of DNA in a urine matrix is both efficient and sensitive, with a broad dynamic range.

3.13 Representative DNA Isolation Method and Results: Example 13

Figure 16:
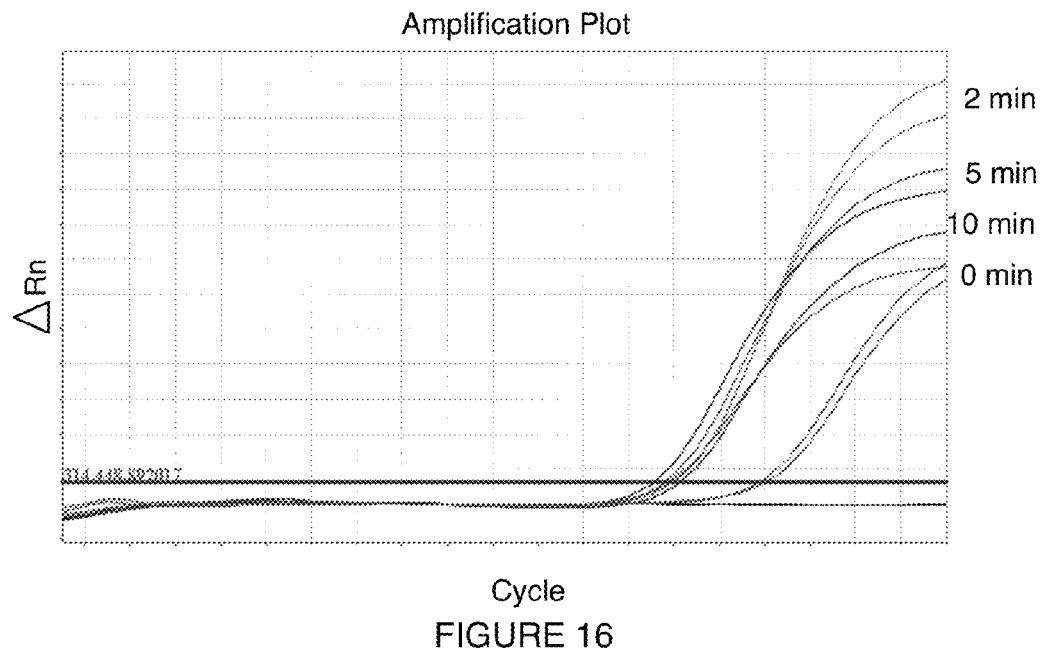
FIG. 16 demonstrates the influence of binding time on the performance of an embodiment of a nucleic acid isolation technique.

A thirteenth example of the method 100, demonstrating the effect of binding time, comprises using PAA affinity moieties coated onto magnetic microparticles, Human Plasma (donor) as a representative biological sample and Group B *Streptococcus* (GBS) DNA (ATCC, Virginia) as the model target. In the thirteenth example, 500 μL of Plasma was spiked with mpg of GBS DNA and then mixed with 500 μL of DNA Collection Buffer 2 (CBD-2) in examples of Steps S110 and S120. DNA was allowed to bind to the PAA affinity moieties coated onto magnetic microparticles for 0, 2, 5, or 10 minutes at room temperature in examples of Step S130. Upon removal of the unbound supernatant in an example of Step S140, the magnetic microparticles with bound DNA were washed with 500 μL of WSH-1 solution in an example of Step S150, and the captured DNA was eluted from the affinity matrix by using ELU-2 and heating the microparticles to 85 C for 3 minutes in an example of Step S160. DNA was eluted into 10 μL of ELU-2 and 8 μL of the eluate was used for real-time PCR in an example of Step S170. As shown in FIG. 16, results of the DNA isolation as elucidated by a GBS real-time PCR assay indicate that the NA isolation reagents are efficacious at capture, release and cleanup of the target DNA in plasma matrix at binding times at or above two minutes in the example method 100.

3.14 Representative DNA Isolation Method and Results: Example 14

Figure 17:
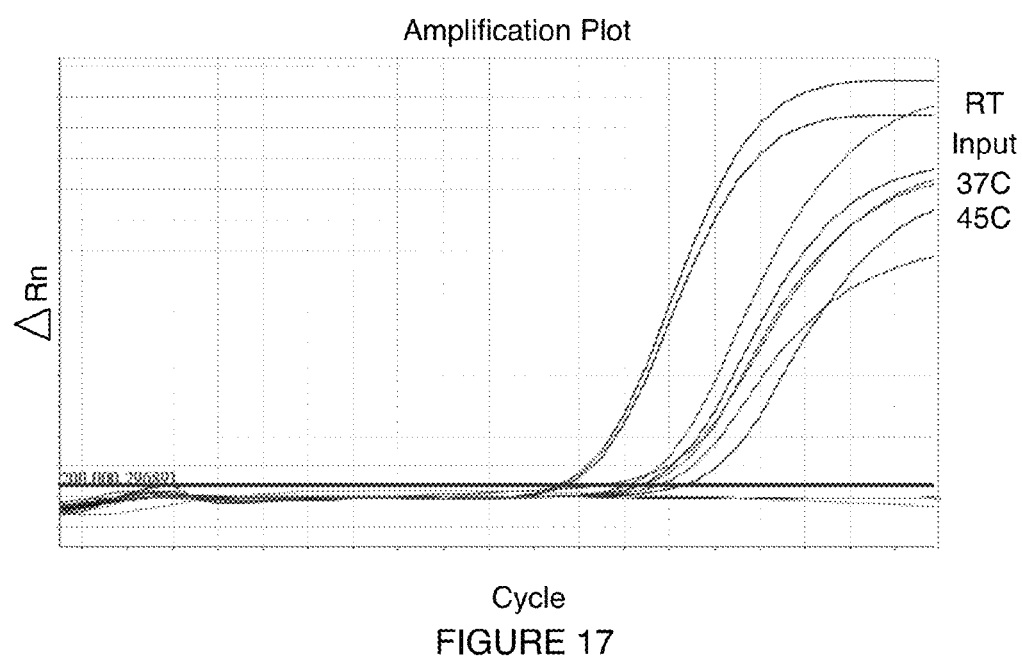
FIG. 17 demonstrates the influence of binding temperature on the performance, in Human Plasma specimens, of an embodiment of a nucleic acid isolation technique.

A fourteenth example of the method 100, demonstrating the effect of binding temperature, comprises using PAA affinity moieties coated onto magnetic microparticles, Human Plasma (donor) as a representative biological sample and Group B *Streptococcus* (GBS) DNA (ATCC, Virginia) as the model target. In the fourteenth example, 500 μL of Plasma was spiked with mpg of GBS DNA and then mixed with 500 μL of DNA Collection Buffer 2 (CBD-2) in examples of Steps S110 and S120. DNA was allowed to bind to the PAA affinity moieties coated onto magnetic microparticles for 10 minutes at room temperature, 37 C, 45 C, or 60 C in examples of Steps S130. Upon removal of the unbound supernatant in an example of Step S140, the magnetic microparticles with bound DNA were washed with 500 μL of WSH-1 solution in an example of Step S150 and the captured DNA was eluted from the affinity matrix by using ELU-2 and heating the microparticles to 85 C for 3 minutes in an example of Step S160. DNA was eluted into 10 μL of ELU-2 and 8 μL of the eluate was used for real-time PCR in an example of Step S170. As a comparison, a similar amount of GBS DNA was used directly in real-time PCR as a reference, which would correlate to an extraction efficiency of 100%. As shown in FIG. 17, results of the DNA isolation as elucidated by a GBS real-time PCR assay indicate that the example method 100 and nucleic acid isolation reagents are efficacious at capture, release and cleanup of the target DNA in plasma matrix at binding temperatures between room temperature and 45 C.

Preferably, variations of the method 100 for plasma nucleic acid extractions comprise eluting into a 20 uL elution volume, providing 40 uL of 20 mg/mL Proteinase K in a lysis solution, providing a salt wash (e.g. 150 mM NaCl in 1 mM Tris pH 8.0), using AptaTaq polymerase, and providing a longer elution time (e.g., 5-10 minutes). However, in other variations of the twelfth through fourteenth examples, the example method 100 can comprise any suitable combination of: using any suitable volume of an elution solution (e.g., 10 uL-25 uL elution solution), providing any suitable composition of an elution solution (e.g., 20 mM NaOH, 40 mM NaOH, KOH), providing a lysis solution with any suitable amount of Proteinase K (e.g., +/−20-40 uL of 20 mg/mL Proteinase K), using any suitable polymerase (e.g., Native Taq, AptaTaq), using fresh or frozen plasma, eluting at any suitable temperature (e.g., room temperature to 85 C), using magnetic microparticles of any hydrophilicity (e.g., hydrophilic, hydrophobic), using any suitable amount of affinity moiety (e.g., 100-3000 ug of PAA) in any suitable volume (e.g., 30 uL), providing any suitable wash solution (e.g, 1 mM TRIS pH 8 with 50-200 mM NaCL, 200 mM KCl in 10 mM TRIS pH 8, 10 mM TRIS pH 8 with 0.1% tween and 1M NaCl, 0.5% SDS in 1 mM TRIS pH 8, 200 mM NaCl in 1 mM TRIS pH 8), resuspending magnetic microparticles in a release buffer, not resuspending magnetic microparticles in a release buffer, and providing any suitable denaturation temperatures (e.g., 85-95 C) and/or anneal temperatures (55-60 C) during processing for PCR.

3.15 Representative DNA Isolation Method and Results: Example 15

Figure 18:
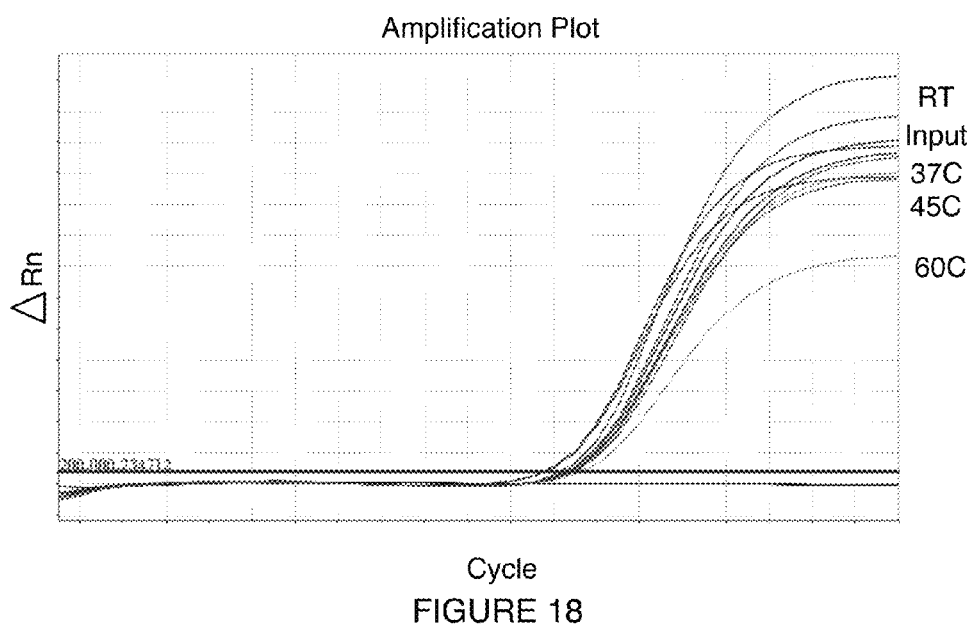
FIG. 18 demonstrates the influence of binding time on the performance, in Human Urine specimens, of an embodiment of a nucleic acid isolation technique.

A fifteenth example of the method 100, demonstrating the effect of binding temperature, comprises using PAA affinity moieties coated onto magnetic microparticles, Urine (donor) as a representative biological sample and Group B *Streptococcus* (GBS) DNA as the model target. In the fifteenth example, 500 μL of Urine (obtained from a donor) was spiked with mpg of GBS DNA and then mixed with 500 μL of DNA Collection Buffer 2 (CBD-2) in examples of Steps S110 and S120. DNA was allowed to bind to the PAA affinity moieties coated onto magnetic microparticles for 10 minutes at room temperature, 37 C, 45 C, or 60 C in examples of Step S130. Upon removal of the unbound supernatant in an example of Step S140, the magnetic microparticles with bound DNA were washed with 500 μL of WSH-1 solution in an example of Step S150, and the captured DNA was eluted from the affinity matrix by using ELU-2 and heating the microparticles to 85 C for 3 minutes in an example of Step S160. DNA was eluted into 10 μL of ELU-2 and 8 μL of the eluate was used for real-time PCR in an example of Step S170. As a comparison, a similar amount of GBS DNA was used directly in real-time PCR as a reference, which would correlate to an extraction efficiency of 100%. As shown in FIG. 18, results of the DNA isolation as elucidated by a GBS real-time PCR assay indicate that the example method 100 and nucleic acid isolation reagents are efficacious at capture, release and cleanup of the target DNA in urine matrix at binding temperatures between room temperature and 60 C.

In other variations of the fifteenth example, the example method 100 can comprise any suitable combination of: providing a lysis solution with any suitable amount of Proteinase K (e.g., +/−20-40 uL of 20 mg/mL Proteinase K) and providing any suitable wash solution (e.g, 1 mM TRIS pH 8, 150 mM NaCl).

3.16 Representative DNA Isolation Method and Results: Example 16

Figure 19:
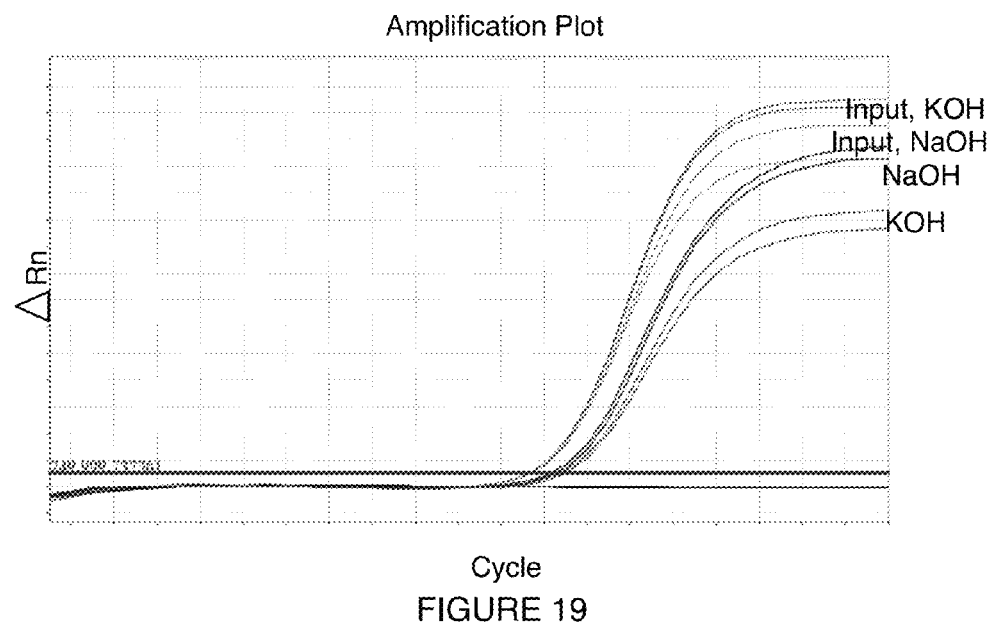
FIG. 19 demonstrates the use of TWO example different elution solutions—NaOH and KOH—on the performance, in Human Urine specimens, of an embodiment of a nucleic acid isolation technique.

A sixteenth example of the method 100, demonstrating the use of two different elution solutions, comprises using PAA affinity moieties coated onto magnetic microparticles, Human Urine (donor) as a representative biological sample and Group B *Streptococcus* (GBS) DNA as the model target. In the sixteenth example, 500 μL of Urine (obtained from donor) was spiked with mpg of GBS DNA and then mixed with 500 μL of DNA Collection Buffer 2 (CBD-2) in examples of Steps S110 and S120. DNA was allowed to bind to the PAA affinity moieties coated onto magnetic micropar-ticles for 10 minutes at room temperature in an example of Step S130. Upon removal of the unbound supernatant in an example of Step S140, the magnetic microparticles with bound DNA were washed with 500 μL of WSH-1 solution in an example of Step S150 and the captured DNA was eluted from the affinity matrix by using ELU-2 or ELU-3 and heating the microparticles to 85 C for 3 minutes in an example of Step S160. DNA was eluted into 10 μL of ELU-2 or ELU-3 and 8 μL of the eluate was used for real-time PCR in an example of Step S170. As a comparison, a similar amount of GBS DNA was used directly in real-time PCR as a reference, which would correlate to an extraction efficiency of 100%. As shown in FIG. 19, results of the DNA isolation as elucidated by a GBS real-time PCR assay indicate that the DNA isolation process is efficient in the biological sample matrix as compared to the input PCR control sample that was not subjected to the full extraction process. A small shift in the amplification of the extracted samples does not necessarily indicate a loss in extraction efficiency or sensitivity. This indicates that the example method 100 and nucleic acid isolation reagents are efficacious at capture, release and cleanup of the target DNA in urine matrix using either NaOH or KOH.

In other variations of the sixteenth example, the example method 100 can comprise any suitable combination of: providing a lysis solution with any suitable amount of Proteinase K (e.g., +/−20-40 uL of 20 mg/mL Proteinase K) and providing any suitable wash solution (e.g., 1 mM TRIS pH 8, 150 mM NaCL).

3.17 Representative RNA and DNA Isolation Method and Results: Example 17

Figure 20:
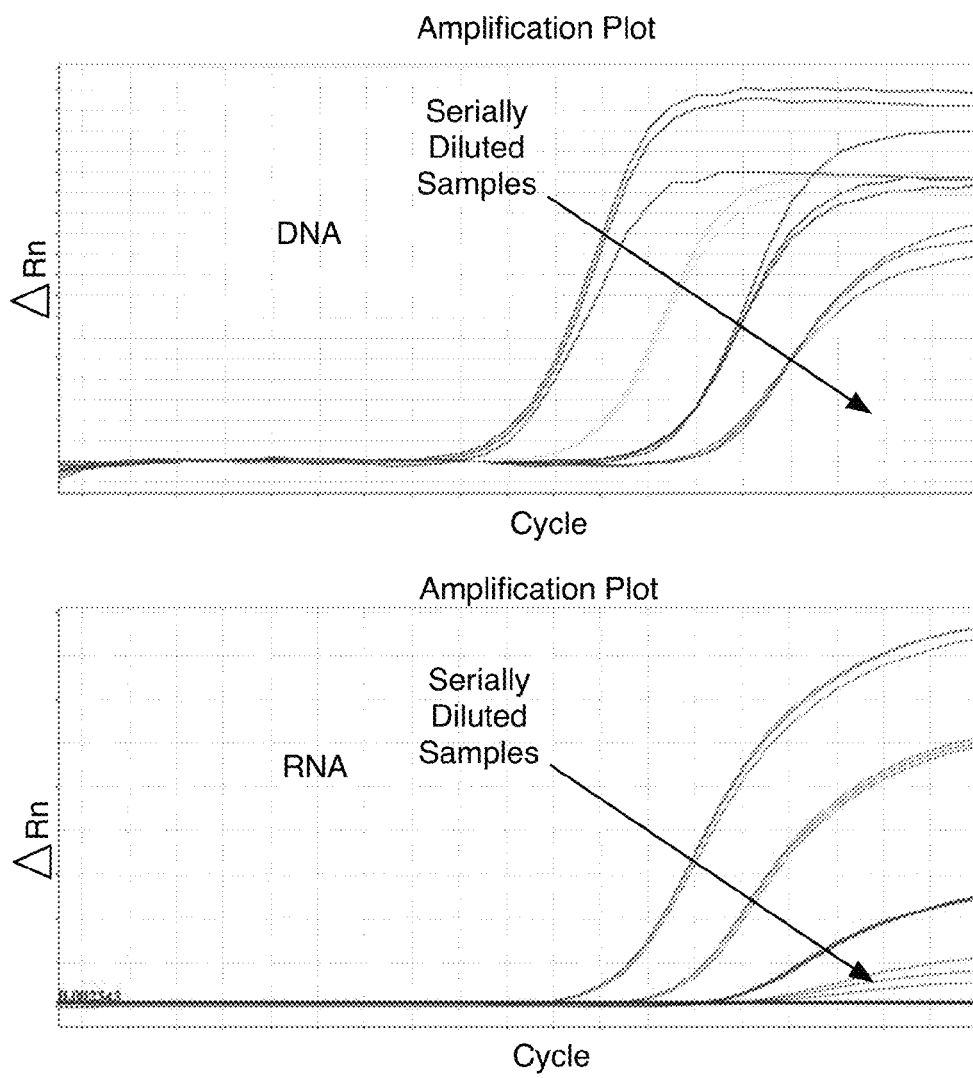
FIG. 20 demonstrates the use of nucleic acid isolation reagents and an embodiment of a process to simultaneously isolate and purify *Enterovirus* RNA and Group B *Streptococcus* DNA using PAA affinity particles, from the same sample matrix, M4 Transport Medium.

A seventeenth example of the method 100, demonstrating the use of nucleic acid isolation reagents for total nucleic acid (TNA) extraction, comprises using PAA affinity moieties coated onto magnetic microparticles, M4 transport media as a representative biological sample, and *Enterovirus* (EV) viral particles as the model RNA target and Group B *Streptococcus* DNA as model DNA target. In the seventeenth example, 500 μL of M4 was spiked with ten-fold serial dilutions of 1 μL of EV viral particle lysate and 1 μL of GBS DNA and then mixed with 500 μL of RNA Collection Buffer 3 (CBR-3) in examples of Steps S110 and S120. RNA and DNA were allowed to bind to the PAA affinity moieties for 10 minutes at 37 C in an example of Step S130. Upon removal of the unbound supernatant in an example of Step S140, the PAA affinity moieties coated onto magnetic microparticles were washed twice (2×) with 500 μL of WSH-1 solution in an example of Step S150, and then the captured RNA and DNA was eluted from the affinity matrix by using ELU-2 at 85 C for 3 minutes in an example of Step S160. The eluate was divided and 2 μL was used for either real-time PCR for GBS target or real-time RT-PCR for EV RNA target in examples of Step S170. As shown in FIG. 20, results of the TNA isolation as evidenced by standard curves produced from a real-time *Enterovirus* RT-PCR assay and real-time GBS assay indicate that the example method 100 and nucleic acid isolation process is equally efficient in purification of RNA or DNA from the same sample.

3.18 Fluidic Pathway: Example 18

Figure 21A:
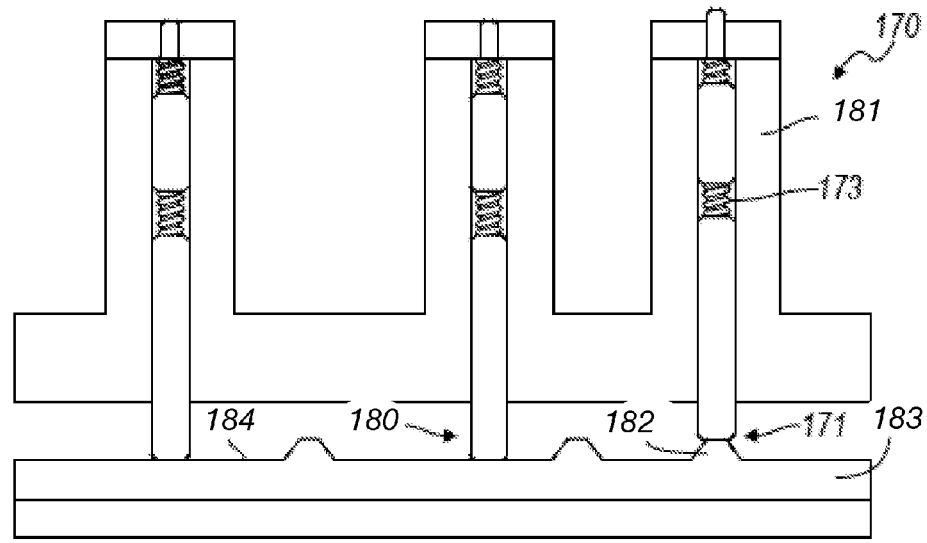
FIGS. 21A-21C depict an example of a valve actuation subsystem of a molecular diagnostic module.
Figure 21B:
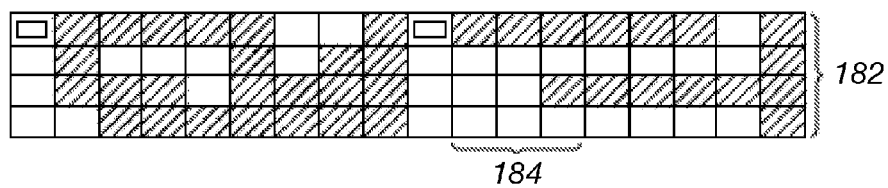
Figure 21C:
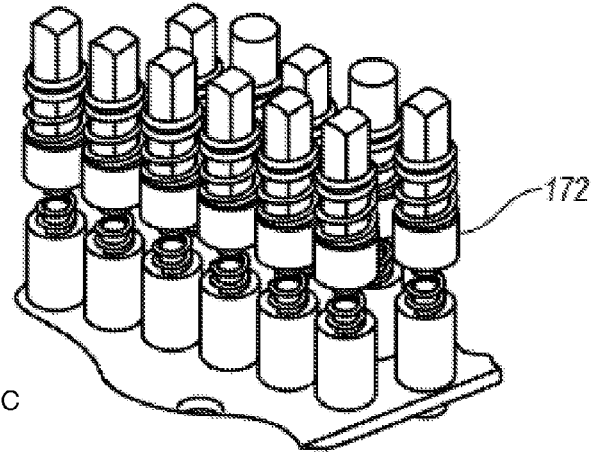

An eighteenth example of the method 100 comprises a set of pins (such as that described in U.S. patent application Ser. No. 13/766,359 (U.S. Pat. App. Pub. No. 2013/0210127 A1), entitled "System and Method for Processing and Detecting Nucleic Acids," and U.S. patent application Ser. No. 13/765, 996 (U.S. Pat. App. Pub. No. 2013/0210125 A1), entitled "Microfluidic Cartridge for Processing and Detecting Nucleic Acids"), the set of pins 172 functions to selectively occlude portions of a fluidic pathway 220 of a microfluidic cartridge 210 at least at subsets of a set of occlusion positions 226. The pins of the set of pins 172 are preferably cylindrical and, in the orientation shown in FIG. 21A, configured to slide over a cam card 183 and within a pin housing 181. Each pin in the set of pins 172 preferably also includes a first spring 173 that functions to provide a counteracting force to restore a pin to a lowered configuration 183b; however, each pin in the set of pins 172 may alternative not include a first spring 173, and rely solely on gravity to return to a lowered configuration 183b. Preferably, as shown in FIG. 21C, each pin is also composed of two parts separated by a second spring, which functions to allow sufficient force to fully occlude a microfluidic channel but prevents forces from being generated that could damage the pin, microfluidic cartridge and/or cam card. Each pin also preferably comprises a first region 171 configured to slide within the pin housing 181, and a second region 180 configured to exit the pin housing 181. The second region 180 is preferably of a smaller dimension than the first region 171, such that each pin is constrained by the pin housing 181 to be raised by a limited amount. Alternatively, the first region 171 and the second region 180 may have any appropriate configuration to facilitate raising and lowering of a pin by a fixed amount. In a specific example, the valve actuation subsystem 170 comprises 12 sets of pins 172 configured to selectively occlude 12 fluidic pathways 212 of a microfluidic cartridge 210 aligned within the molecular diagnostic module; however, other embodiments may comprise any appropriate number of sets of pins 172.

The eighteenth example of the method 100 comprises a cam card (such as that described in U.S. patent application Ser. No. 13/766,359 (U.S. Pat. App. Pub. No. 2013/0210127 A1), entitled "System and Method for Processing and Detecting Nucleic Acids"), the cam card 183, as shown in FIG. 21A, includes a set of hills 182 and valleys 184, and functions to transform linear motion in one plane to vertical motion in another plane. In one variation, the cam card 183 is coupled to a linear actuator and contacts the ends of pins in a set of pins 172, such that when a hill 182 of the cam card 183 passes under a pin, the pin is in a raised configuration 183a, and when a valley 184 of the cam card 183 passes under a pin, the pin is in a lowered configuration 183b. The hills 182 and valleys 184 of the cam card 183 are preferably in a set configuration, as shown in FIG. 21B, such that lateral motion of the cam card 183 to a set position raises a fixed subset of the set of pins 172. In this manner, lateral movement of the cam card 183 to different positions of a set of positions consistently raises different subsets of the set of pins 172 to occlude different portions of a fluidic pathway 220 of a microfluidic cartridge 210 in contact with the set of pins 172. Thus, portions of a fluidic pathway 220 may be selectively occluded and opened to facilitate processing of a biological sample according to any appropriate tissue, cellular, or molecular diagnostic assay protocol. In one variation, the cam card is configured to be laterally displaced in two coordinate directions within a plane (e.g., by x-y linear actuators), and in another variation, the cam card is configured to be laterally displaced in only one coordinate direction within a plane (e.g., by a single linear actuator). In a specific example, the hills 182 of the cam card 183 are raised 1 mm above the valleys 184 of the cam card 183, the hills 182 and valleys 184 each have a 2 mm wide plateau region, and a hill 182 region slopes down to a valley region 184 at a fixed angle over a 2 mm length. In the specific example, the cam card 183 is driven by a Firgelli linear actuator. Alternative variations may include any appropriate configurations and geometries of a cam card with hills 182 and valleys 184, driven by any appropriate actuator.

Figure 22A:
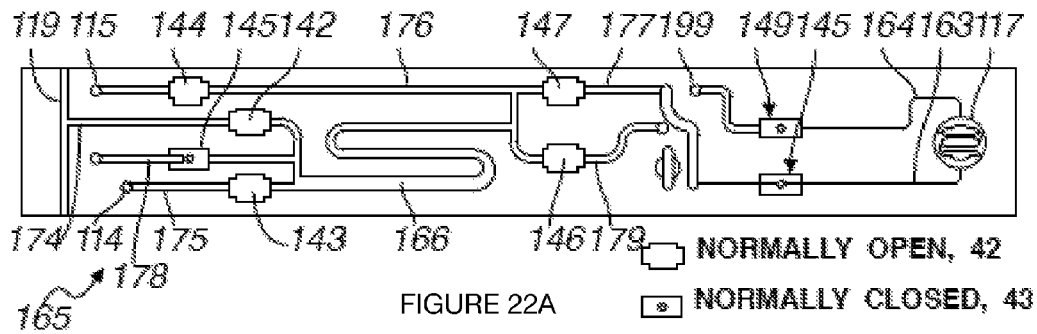
FIGS. 22A-22C depict an example of subsets of occlusion positions defining truncated portions of a fluidic pathway.

A first illustration of the eighteenth example, as shown in FIG. 22A, of a fluidic pathway 165 preferably comprises an initial segment 174 fluidically coupled to a fluid channel 119 coupled to a shared fluid port 118, a sample segment 175 coupled to a sample port 114 and to the initial segment 174, and an s-shaped capture segment 166, configured to pass through the heating region 195 and a magnetic field 156, coupled to the initial segment 174 and the sample segment 175. In an alternative illustration of the eighteenth example, the s-shaped capture segment 166 may comprise an initial wide arc 166 to provide a greater surface area for magnetic bead capture. In another illustration of the eighteenth example, the capture segment 166 may alternatively be a progressively narrowing s-shaped capture segment 166. The first illustration of the fluidic pathway 165 also comprises a reagent segment 176 coupled to a reagent port 115 and to the capture segment 166, a vent segment 177 coupled to the reagent segment 176 and configured to pass through the vent region 190, a segment running to a detection chamber 163 from the vent region 190, a winding segment running away from the detection chamber 164, and an end vent 199 coupled to the segment running away from the detection chamber 164. The first illustration of the fluidic pathway 165 also comprises a first waste segment 178 configured to couple the initial segment 174 to the waste chamber 130, and a second waste segment 179 configured to couple the capture segment 166 to the waste chamber 130. The first waste segment 178 preferably functions to allow evacuation of excess release fluids from a fluidic pathway 165, for precise metering of the amount of release reagents used in a molecular diagnostic procedure using a low volume of sample.

In the first illustration, the set of occlusion positions 141 comprises a first occlusion position 142 located along the initial segment 174 between points at which the initial segment couples to the fluid channel 119 and to the capture segment 166. The set of occlusion positions 141 also comprises a second occlusion position 143 located along the sample segment 175, a third occlusion position 144 located along the reagent segment 176, a fourth occlusion position 145 located along the first waste segment 178, and a fifth occlusion position 146 located along the second waste segment 179. In the first illustration, the set of occlusion positions 141 also comprises a sixth occlusion position 147 located along the vent segment 177 upstream of the vent region 190, a seventh occlusion position 148 located along the segment running to the detection chamber 163, and an eighth occlusion position 149 located along the segment running away from the detection chamber 164. In the first illustration, the first, second, third, fifth, and sixth occlusion positions 142, 143, 144, 146, 147 are normally open positions 42 and the fourth, seventh, and eighth occlusions positions 145, 148, 149 are normally closed positions 43, as shown in FIG. 22A.

Figure 22B:
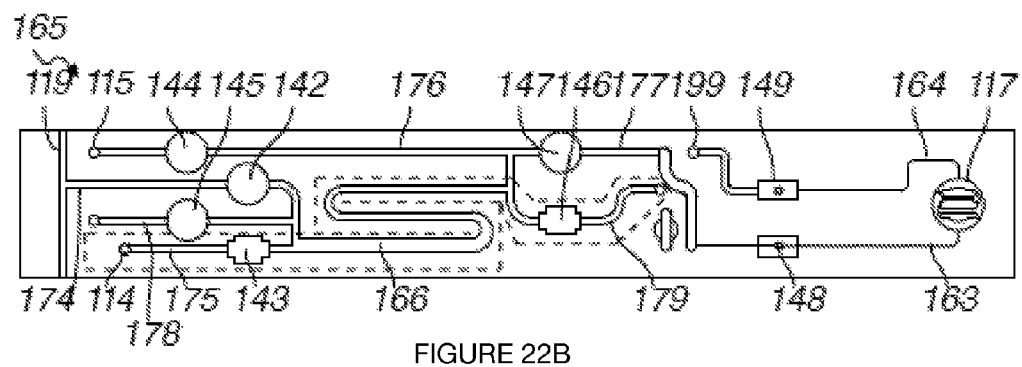
Figure 22C:
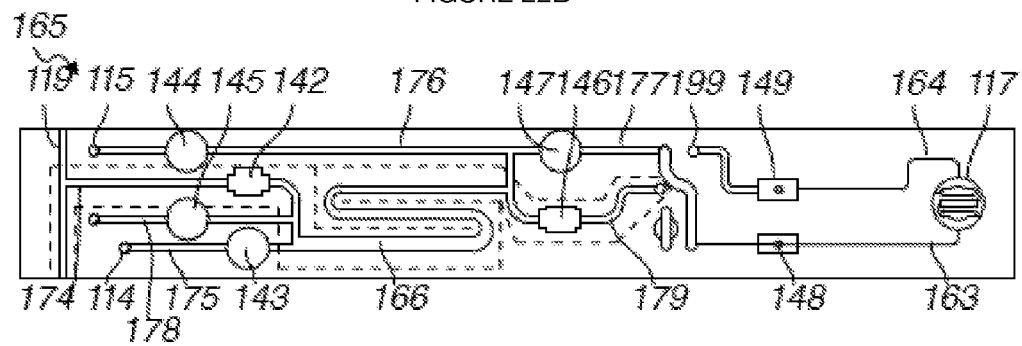

The occlusion positions of the set of occlusion positions 141 of the first illustration are preferably located such that occluding subsets of the set of occlusion positions 141 defines unique truncated fluidic pathways to controllably direct fluid flow. For example, as shown in FIG. 22B, occluding the fluidic pathway 165 at the first, third, fourth, and sixth occlusion positions 142, 144, 145, 147 forms a truncated pathway by which a volume of a sample fluid, comprising nucleic acids bound to magnetic beads and delivered into the sample port 114, may flow past the second occlusion positions 143 into the capture segment 166 for isolation and purification of nucleic acids using the heating region 195 and the magnetic field 156. Nucleic acids bound to magnetic beads may thus be trapped within the capture segment 166 by the magnetic field 156, while other substances in the volume of sample fluid may pass into the waste chamber 130 by passing the fifth occlusion position 146. Following this subset of occlusion positions, the occlusion at the first occlusion position 142 may be reversed, as shown in FIG. 22C, and the fluidic pathway 165 may be occluded at the second occlusion position 143 to form a second truncated pathway by which a wash fluid may be delivered through the fluid port 118, into the capture segment 166 (thus washing the trapped magnetic beads), and into the waste chamber 130 by passing the fifth occlusion position 146. The occlusion at the second occlusion position 143 may then be reversed, and the first occlusion position 142 may be occluded (as shown in FIG. 22B), so that other fluidic pathways in the set of fluidic pathways 160 may be washed. After all fluidic pathways have been washed, a volume of air may be transferred through the fluid port 118 to prevent mixture of a wash solution with a release solution.

Thereafter in the first illustration, as shown in FIG. 22C, the fluidic pathway 165 may be occluded at the second occlusion position 143 and the occlusion at the first occlusion 142 may be reversed, thus creating a third truncated pathway as shown in FIG. 22B. A release solution may then be delivered through the fluid port 118, into the capture segment 166, and to the waste chamber 130 by passing the fifth occlusion position 146. The release solution may then be sealed within a fourth truncated pathway (including the capture segment 166) of the fluidic pathway 165 by occluding the fluidic pathway at the fifth occlusion position 146. A release solution may then be delivered to other fluidic pathways of the set of fluidic pathways 160.

Thereafter, the occlusion at the fourth occlusion position 145 maybe reversed, creating a fifth truncated pathway, and release solution within the fluidic pathway 165 may be metered by pumping air through the fluid port 118, which functions to push a portion of the release solution into the waste chamber 130. A volume of release solution will still be maintained within the capture segment 166 at this stage. The first and the fourth occlusion positions 142, 145 may then be occluded to form a sixth truncated pathway sealing the volume of release solution, with the captured magnetic beads bound to nucleic acids, within the capture segment 166. The volume of the remaining release solution is therefore substantially defined by the microchannel volume between junctions in the fluidic pathway 165 near the fourth and sixth occlusion positions 145, 147, and maybe any small volume but in a specific variation is precisely metered to be 23+/−1 microliters. Release solution may be sealed within capture segments of other fluidic pathways using a similar process. A heater may then be provided at the sixth truncated pathway, inducing a pH shift within the sixth truncated pathway to unbind nucleic acids from the magnetic beads.

Thereafter in the first illustration, the occlusions at the first and third occlusion positions 142, 144 may be reversed, defining a seventh truncated pathway, and the entire released nucleic acid sample (e.g. ~20 microliters) may be aspirated out of the microfluidic cartridge through the reagent port 115. This released nucleic acid sample is then used to reconstitute a molecular diagnostic reagent stored off of the microfluidic cartridge 100. During the reconstitution, the occlusion at the sixth occlusion position 147 may be reversed, and the fluidic pathway 165 may be occluded at the first occlusion position 142 to form an eighth truncated pathway. Once reconstitution of the molecular diagnostic reagent with the released nucleic acid sample is complete and well mixed, the reconstituted mixture may then be dispensed through the reagent port 115, through the eighth truncated pathway, and to the detection chamber 117, by using a fluid handling system to push the seventh occlusion position (normally closed) open. The detection chamber 117 is completely filled with the mixed reagent-nucleic acid sample, after which the fluidic pathway 165 is occluded at the third, sixth, seventh and eighth occlusion positions 144, 147, 148, 149, defining ninth truncated pathway. Other pathways of the set of fluidic pathways 165 may be similarly configured to receive a reagent-nucleic acid mixture. An external molecular diagnostic system and/or module may then perform additional processes, such as thermocycling and detection, on the volume of fluid within the detection chamber 117.

An alternative illustration of the eighteenth example may further comprise additional occlusion positions or alternative variations of the set of occlusion positions 141, such that occlusion at the additional occlusion positions permanently seals the waste chamber from the fluidic pathway 165. Other alternative illustrations of the eighteenth example may also comprise configurations of the set of occlusion positions 141 that are different than that described above. The variations may be configured, such that the a fluidic pathway 165 facilitates meter release, does not allow meter release, facilitates addition of other reagents (e.g. neutralization or DNase reagents), facilitates additional washing steps, and/or facilitates other operations without changing the layout of the fluidic pathway 165 of a microfluidic cartridge embodiment. Thus, multiple unique operations may be performed using the same microfluidic cartridge, by occluding fluidic pathways 160 at varied subsets of a set of occlusion positions 141.

A second illustration of the eighteenth example, of a fluidic pathway 165' preferably comprises an initial segment 174 ' fluidically coupled to a fluid channel 119' coupled to a shared fluid port 118', a sample segment 175' coupled to a sample port 114' and to the initial segment 174', and a capture segment 166', configured to pass through the heating region 195 and a magnetic field 156, coupled to the initial segment 174'. The second illustration of the fluidic pathway 165' also comprises a reagent segment 176' coupled to a reagent port 115' and to the turnabout portion 176', a vent segment 177' coupled to the reagent segment 176' and to the capture segment 166' and configured to pass through the vent region 190, a segment running to a detection chamber 163' from the vent region 190, a segment running away from the detection chamber 164', and an end vent 199 coupled to the segment running away from the detection chamber 164'. The second illustration of the fluidic pathway 165' also comprises a first waste segment 178', coupled to the initial segment 174' at a point between points connecting the initial segment 174' to the sample segment 175' and to the capture segment 166'. The first waste segment 178' is configured to couple the initial segment 174' to the waste chamber 130. The second illustration of the fluidic pathway 165' also comprises a second waste segment 179' configured to couple the capture segment 166' to the waste chamber 130', and an end vent segment 197' coupled to the capture segment 166' downstream of the point of connection to the second waste segment 179', and coupled to an end vent 199. The end vent segment 197' functions to provide fine metering of a fluid flowing through the fluidic pathway 165'.

In the second illustration, the set of occlusion positions 141' comprises a first occlusion position 142' located along the initial segment 174' between points at which the initial segment couples to the fluid channel 119' and to the sample segment 175'. The set of occlusion positions 141' also comprises a second occlusion position 143' located along the sample segment 175', a third occlusion position 144' located along the reagent segment 176', a fourth occlusion position 145' located along the first waste segment 178', and a fifth occlusion position 146' located along the second waste segment 179'. In the second illustration, the set of occlusion positions 141' also comprises a sixth occlusion position 147' located along the vent segment 177' upstream of the vent region 190, a seventh occlusion position 148' located along the segment running to the detection chamber 163', and an eighth occlusion position 149' located along the segment running away from the detection chamber 164'. Additionally, in the second illustration, the set of occlusion positions 141 comprises a ninth occlusion position 157' located along the sample segment 175' between the sample port 114 and the second occlusion position 143, a tenth occlusion position 158' located along the end vent segment 197', and an eleventh occlusion position 159' located along the capture segment 166' between points at which the capture segment 166' couples to the end vent segment 197' and to the vent segment 177'.

The occlusion positions of the set of occlusion positions 141' of the second illustration are preferably located such that occluding of subsets of the set of occlusion positions 141' defines unique truncated fluidic pathways to controllably direct fluid flow. For example, occluding the fluidic pathway 165' at the first, fourth, sixth, tenth, and eleventh occlusion positions 142', 145', 147', 158', 159' forms a truncated pathway by which a volume of a sample fluid, comprising nucleic acids bound to magnetic beads and delivered into the sample port 114, may flow into the capture segment 166' for isolation and purification of nucleic acids using the heating region 195 and the magnetic field 156. Nucleic acids bound to magnetic beads may thus be trapped within the capture segment 166' by the magnetic field 156, while other substances in the volume of sample fluid may pass into the waste chamber 130 by passing the fifth occlusion position 146'. Following this subset of occlusion positions, the occlusion at the first occlusion position 142' may be reversed, and the fluidic pathway 165' may be occluded at the second occlusion position 143' to form a second truncated pathway by which a wash fluid may be delivered through the fluid port 118, into the capture segment 166' (thus washing the trapped magnetic beads), and into the waste chamber 130 by passing the fifth occlusion position 146'. A volume of air may then be pumped through the fluid port 118 to flush any remaining wash solution into the waste chamber 130.

Thereafter, in the second illustration, the fluidic pathway 165' may be occluded at the fifth occlusion position 146' and the occlusion at the tenth occlusion position 158' may be reversed, closing access to the waste chamber 130 and opening access to the end vent segment 197'. A release solution may then be delivered through the fluid port 118, into the capture segment 166', and to the end vent segment 197'. The volume of the release solution is therefore defined by the microchannel volume between the fourth and tenth occlusion positions 145', 158', and maybe any small volume but in a specific variation is precisely metered to be 15 microliters. Thereafter, occluding the fluidic pathway 165' at the tenth occlusion position 158', reversing the occlusion at the fourth occlusion position 145' (defining a fourth truncated pathway), and delivering air through the fluid port 118 pushes any remaining release buffer from the fluidic pathway 118 into the waste chamber 130, thereby ensuring that excess release buffer is not later exposed to nucleic acids bound to the magnetic beads (at this point, the nucleic acids are not substantially released from the magnetic beads because heat has not been added). Thereafter, the fluidic pathway 165' is occluded at the first and fourth occlusion positions 142', 145', defining a fifth truncated pathway comprising the capture segment 166', and the magnetic beads are heated to an appropriate temperature and time (e.g., 60 degrees for 5 minutes) within the heating region 195 to release the nucleic acids from the magnetic beads and into the release buffer.

Thereafter, in the second illustration, the occlusions at the first and eleventh occlusion positions 142', 159' are reversed, defining a sixth truncated pathway, the entire released nucleic acid sample (e.g. ~15 microliters) may be aspirated out of the microfluidic cartridge through the reagent port 115. This released nucleic acid sample is then used to reconstitute a molecular diagnostic reagent mixture stored off of the microfluidic cartridge 100. During the reconstitution process, the occlusion at the sixth occlusion position 147' may be reversed, thus defining a seventh truncated pathway. Once reconstitution of the molecular diagnostic reagent mixture with the released nucleic acid sample is complete and well mixed, the reconstituted mixture may then be aspirated through the reagent port 115 through the seventh truncated pathway to the detection chamber 117, completely filling the detection chamber 117, after which the fluidic pathway 165' is be occluded at third, seventh, eighth, and ninth occlusion positions 144', 148', 149', 157' defining an eighth truncated pathway. An external molecular diagnostic system and/or module may then perform additional processes on the volume of fluid within the detection chamber 117.

An alternative illustration of the eighteenth example may further comprise additional occlusion positions or alternative variations of the set of occlusion positions 141', such that occlusion at the additional occlusion positions permanently seals the waste chamber from the fluidic pathway 165'. Other alternatives of the second illustration may also comprise configurations of the set of occlusion positions 141' that are different than that described above.

4. Example Reagents Used in the Example Methods

The following example reagent formulations were used the examples described in Sections 30.1-3.17. Quantities in parentheses following component names denote quantities used to form a 1 liter volume of a respective reagent formulation.

CBR-1 [2×TCEP Buffer] Formulation: ultrapure water (946 mL), 1M Tris pH 7.0 (20 mL), Tris(2-carboxyethyl) phosphine hydrochloride, or TCEP, (14.3 g), and Triton-X 100 (20 mL).

CBR-2[2× Low TCEP Buffer] Formulation (1 L): ultrapure water (959 mL), 1M Tris pH 8.0 (20 mL), TCEP (1.43 g), and Triton-X 100 (20 mL).

CBR-3 [2× EDTA only Buffer]: ultrapure water (560 mL), 1M Tris pH 8.0 (20 mL), 0.5M EDTA pH 8.0 (400 mL), and Triton-X 100 (20 mL).

CBD-1 [SP1]: ultrapure water (931 mL), 1M Tris pH 7.0 (50 mL), sodium citrate (50.88 g), boric acid (1.24 g), 0.5M EDTA pH 8.0 (2 mL), and Triton-X 100 (10 mL).

CBD-2 [SP2]: ultrapure water (480 mL), 1M Tris pH 7.0 (100 mL), sodium citrate (11.76 g), boric acid (2.48 g), 0.5M EDTA pH 8.0 (400 mL), and Triton-X 100 (20 mL).

CBD-3 [SP3]: ultrapure water (862 mL), 1M Tris pH 7.0 (100 mL), sodium citrate (11.76 g), boric acid (2.48 g), 0.5M EDTA pH 8.0 (4 mL), and Triton-X 100 (20 mL).

CBD-4 [TT]: ultrapure water (978 mL), 1M Tris pH 8.0 (2 mL), and Triton-X 100 (20 mL).

Wash Solution [WSH-1]: ultrapure water (999 mL) and 1M Tris pH 8.0 (1 mL).

Elution Solution [ELU-1] —20 mM NaOH: ultrapure water (980 mL) and 1N NaOH (20 mL).

Elution Solution [ELU-2] —40 mM NaOH: ultrapure water (960 mL) and 1N NaOH (40 mL).

Elution Solution [ELU-3]—40 mM KOH: ultrapure water (960 mL) and 1N KOH (40 mL).

The methods 100, 200 and system of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of molecular diagnostics will recognize from the previous detailed description and from the figures and claims, modifications and changes can be made to the preferred embodiments of the invention without departing from the scope of this invention defined in the following claims.

We claim:

1. A method for nucleic acid isolation comprising:
    receiving a binding moiety solution within a process chamber, wherein the binding moiety solution comprises a collection buffer and a set of affinity moiety-coated microparticles, wherein the set of affinity moiety-coated microparticles comprises Polypropylenimine tetramine dendrimer Generation 1 amide-bonded to a set of microparticles;
    contacting the binding moiety solution with a biological sample, within the process chamber, thereby producing a moiety-sample mixture;
    incubating the moiety-sample mixture to reversibly bind nucleic acid material of the biological sample to the set of affinity moiety-coated microparticles, thereby producing a set of moiety-bound nucleic acid particles;
    receiving a cartridge at a cartridge receiving module comprising a set of pins, each pin in the set of pins displaceable between a first position and a second position;
    occluding a fluidic pathway of the cartridge upon displacement of a first subset of the set of pins;
    separating the set of moiety-bound nucleic acid particles from the moiety-sample mixture, within the fluidic pathway of the cartridge;
    washing the set of moiety-bound nucleic acid particles within the fluidic pathway of the cartridge, in coordination with displacement of a second subset of the set of pins, wherein displacement of the second subset of pins includes reversal of displacement of at least one pin in the first subset of the set of pins, in reversing occlusion of a portion of the fluidic pathway; and
    releasing a nucleic acid sample from the set of moiety-bound nucleic acid particles with an elution solution characterized by a pH greater than 10.

2. The method of claim 1, wherein receiving the binding moiety solution, comprising the set of affinity moiety-coated microparticles, within the process chamber comprises receiving a set of magnetic microparticles, each magnetic microparticle modified with an amine-reactive ester functional group configured to react with one of a set of amine groups of a molecule of Polypropylenimine tetramine dendrimer Generation 1.

3. The method of claim 1, wherein receiving the binding moiety solution, comprising the set of affinity moiety-coated microparticles, comprises receiving a set of magnetic microparticles covalently bonded to a set of affinity moiety molecules, and wherein contacting the binding moiety solution with the biological sample comprises aspirating the binding moiety solution along with the biological sample from the process chamber and dispensing the binding moiety solution with the biological sample to the process chamber.

4. The method of claim 3, wherein incubating the moiety-sample mixture comprises heating the moiety-sample solution to a temperature in the range of 25-95° C. for 5-60 minutes, thus simultaneously lysing the biological sample and facilitating binding of nucleic acid material of the biological sample to the set of affinity moiety-coated microparticles.

5. The method of claim 3, wherein separating the set of moiety-bound nucleic acid particles from the moiety-sample mixture comprises magnetically separating the set of moiety-bound nucleic acid particles from the moiety-sample mixture.

6. The method of claim 5, wherein magnetically separating the set of moiety-bound nucleic acid particles from the moiety-sample mixture comprises aspirating the moiety-sample mixture from the process chamber; occluding the fluidic pathway of the cartridge-at a set of occlusion positions upon displacement of pins of the set of pins to generate a path through a magnetic field, and to a waste chamber; and delivering the moiety-sample mixture through the path of the fluidic pathway, such that the set of moiety-bound nucleic acid particles is captured within the magnetic field and a waste volume of the moiety-sample mixture is delivered into the waste chamber.

7. The method of claim 1, wherein separating the set of moiety-bound nucleic acid particles from the moiety-sample mixture comprises at least one of filtering the moiety-sample mixture and focusing the moiety-sample mixture.

8. The method of claim 1 wherein receiving the binding moiety solution comprises receiving a binding buffer that is also configured to aid in lysis of nucleic acid-containing cells of the biological sample, thereby releasing nucleic acid material from the biological sample for binding.

9. The method of claim 1 wherein receiving the binding moiety solution comprises receiving a binding buffer configured to aid in mitigation of nucleolytic activity from the biological sample.

10. The method of claim 3, wherein washing the set of moiety-bound nucleic acid particles comprises aspirating the moiety-sample mixture; receiving the cartridge at the cartridge receiving module comprising the set of pins and a cam card interfacing with the set of pins; transitioning the cartridge to an active configuration that disposes the cartridge proximal the set of pins; displacing the first subset of the set of pins in the active configuration of the cartridge, upon translation of the cam card relative to the set of pins, thereby occluding the fluidic pathway of the cartridge at a set of occlusion positions; delivering the moiety-sample mixture into the fluidic pathway, wherein the fluidic pathway is configured to pass through a magnetic field and is coupled to a waste chamber, such that the set of moiety-bound nucleic acid particles is captured within the magnetic field; and delivering a wash solution through the fluidic pathway and into the waste chamber in a continuous flow operation.

11. The method of claim 1, wherein washing the set of moiety-bound nucleic acid particles comprises transferring the moiety-sample mixture to a fluid vessel, capturing the set of moiety-bound nucleic acid particles within the fluid vessel, and washing the set of moiety-bound nucleic acid particles using a series of aspiration and dispensing steps.

12. The method of claim 11, wherein washing comprises delivering a wash solution through the fluid vessel at a flow rate between 1 and 10 microliters/second, with a total wash solution volume of between 50 and 2000 microliters.

13. The method of claim 3, wherein releasing the nucleic acid sample from the set of moiety-bound nucleic acid particles comprises occluding the fluidic pathway of the cartridge, comprising the process chamber, at a set of occlusion positions, upon displacement of pins of the set of pins, to define a path through a magnetic field; delivering the set of moiety-bound nucleic acid particles into the path of the fluidic pathway; and delivering an elution solution into the fluidic pathway, thereby inducing a pH shift configured to release the nucleic acid sample from the set of moiety-bound nucleic acid particles.

14. The method of claim 13, further comprising capturing the set of moiety-bound nucleic acid particles within the magnetic field and aspirating the nucleic acid sample from the fluidic pathway.

15. The method of claim 1, wherein releasing the nucleic acid sample from the set of moiety-bound nucleic acid particles comprises contacting the set of moiety-bound nucleic acid particles with an elution solution characterized by a pH that is in the range of pH 10 to pH 13.

16. The method of claim 1, further comprising processing the nucleic acid sample, wherein processing the nucleic acid sample comprises modulating the fluidic pathway of the cartridge upon displacement of a third subset of the set of pins, thereby defining a path to a diagnostic chamber of the cartridge, delivering the nucleic acid sample to the diagnostic chamber, and amplifying nucleic acids of the nucleic acid sample within the diagnostic chamber by polymerase chain reaction.

17. A method for total nucleic acid extraction, comprising simultaneous isolation and concentration of DNA and RNA from a biological sample, the method comprising:
receiving a binding moiety solution within a process chamber, wherein the binding moiety solution comprises a collection buffer and a set of affinity moiety-coated microparticles, wherein the set of affinity moiety-coated microparticles comprises Polypropylenimine tetramine dendrimer Generation 1 amide-bonded to a set of magnetic microparticles;
mixing the binding moiety solution with between 10uL and 2mL of a biological sample, within the process chamber, thereby producing a moiety-sample mixture;
incubating the moiety-sample mixture to reversibly bind nucleic acid material, comprising target DNA and RNA, of the biological sample to the set of affinity moiety-coated microparticles, thereby producing a set of moiety-bound nucleic acid particles;
receiving a cartridge at a cartridge receiving module comprising a set of pins, each pin in the set of pins displaceable between a first position and a second position;
occluding a fluidic pathway of the cartridge upon displacement of a first subset of the set of pins;
magnetically separating the set of moiety-bound nucleic acid particles from the moiety-sample mixture, within the fluidic pathway of the cartridge; and
eluting a nucleic acid sample comprising target DNA and RNA from the set of moiety-bound nucleic acid particles, into less than 20uL of an elution solution characterized by a pH greater than 10, in coordination with displacement of a second subset of the set of pins to modulate flow in the fluidic pathway, thereby facilitating total nucleic acid extraction.

18. The method of claim 17, wherein magnetically separating the set of moiety-bound nucleic acid particles from the moiety-sample mixture comprises aspirating the moiety-sample mixture from the process chamber; occluding the fluidic pathway of the cartridge at a set of occlusion positions upon displacement of the first subset of the set of pins to generate a path through a magnetic field, and to a waste chamber of the cartridge; and delivering the moiety-sample mixture through the path of the fluidic pathway, such that the set of moiety-bound nucleic acid particles is captured within the magnetic field and a waste volume of the moiety-sample mixture is delivered into the waste chamber.

19. A method for nucleic acid isolation from a biological sample, comprising:
receiving a binding moiety solution within a process chamber, wherein the binding moiety solution includes a set of affinity moiety-coated microparticles, comprising a set of microparticles amide-bonded to at least one of Poly(allylamine) of molecular weight <30,000 Da and Polypropylenimine tetramine dendrimer Generation 1;
producing a moiety-sample mixture upon combination of the binding moiety solution with the biological sample;
producing a set of moiety-bound nucleic acid particles upon incubation of the moiety-sample mixture to reversibly bind nucleic acid material of the biological sample to the set of affinity moiety-coated microparticles;
receiving a cartridge at a cartridge receiving module comprising a set of pins, each pin in the set of pins displaceable between a first position and a second position;
occluding a fluidic pathway of the cartridge upon displacement of a first subset of the set of pins;
separating the set of moiety-bound nucleic acid particles from the moiety-sample mixture, within the fluidic pathway of the cartridge;
washing the set of moiety-bound nucleic acid particles within the fluidic pathway of the cartridge; and
releasing a nucleic acid sample from the set of moiety-bound nucleic acid particles with an elution solution, in coordination with displacement of a second subset of the set of pins, wherein displacement of the second subset of the set of pins includes reversing displacement of at least one pin of the first subset of the set of pins, and reversing occlusion of a portion of the fluidic pathway.

20. The method of claim 19, wherein occluding the fluidic pathway comprises linearly displacing a cam card of the cartridge receiving module, comprising a set of hills and valleys, relative to the set of pins, wherein displacing the cam card transitions at least one pin of the set of pins between the first position and the second position.

* * * * *